United States Patent
Thompson et al.

(10) Patent No.: US 6,545,139 B1
(45) Date of Patent: Apr. 8, 2003

(54) DNA SEQUENCE ENCODING THE P99 GENE AND KITS FOR THE DETECTION OF NEOPLASIA

(75) Inventors: Timothy C. Thompson, Houston, TX (US); Chengzhen Ren, Rearland, TX (US)

(73) Assignee: Baylor College of Medicine, Houston, TX (US)

(*) Notice: Subject to any disclaimer, the term of this patent is extended or adjusted under 35 U.S.C. 154(b) by 0 days.

(21) Appl. No.: 09/266,764

(22) Filed: Mar. 12, 1999

Related U.S. Application Data

(60) Provisional application No. 60/077,934, filed on Mar. 13, 1998.

(51) Int. Cl.$^7$ .................. C07H 21/04; C07H 21/02; C12H 21/00; C12H 15/09; C12H 15/63

(52) U.S. Cl. .................. 536/23.5; 536/23.1; 536/23.51; 536/23.53; 435/320.1

(58) Field of Search .................. 424/93.21; 536/23.1, 536/23.5, 23.51, 23.53; 435/320.1

(56) References Cited

U.S. PATENT DOCUMENTS

| | | | |
|---|---|---|---|
| 4,317,818 A | 3/1982 | Benson et al. | 424/242 |
| 4,925,835 A | 5/1990 | Heston | 514/183 |
| 5,116,615 A | 5/1992 | Gokcen et al. | 424/94.2 |
| 5,260,224 A | 11/1993 | Stossel et al. | 436/503 |
| 5,633,161 A | 5/1997 | Shyjan | 435/325 |
| 5,783,182 A | 7/1998 | Thompson | 424/93.21 |
| 5,834,234 A | 11/1998 | Gallo | 435/69.1 |

FOREIGN PATENT DOCUMENTS

| | | | | |
|---|---|---|---|---|
| EP | WO 94/16737 | 8/1994 | .......... | A61K/48/00 |
| WO | WO 86/03226 | 6/1986 | .......... | C12N/15/00 |
| WO | WO 94/04196 | 3/1994 | .......... | A61K/48/00 |
| WO | WO 94/28129 | 12/1994 | .......... | C12N/15/12 |
| WO | WO 95/19369 | 7/1995 | .......... | C07H/21/02 |
| WO | WO 96/30389 | 10/1996 | .......... | C07H/21/04 |
| WO | WO 97/09055 | 3/1997 | .......... | A61K/35/42 |
| WO | WO 97/18454 | 5/1997 | | |
| WO | WO 99/22773 | 5/1999 | .......... | A60K/48/00 |

OTHER PUBLICATIONS

Mangelsdorf et. al.; Characterization of three RXR genes that mediate the action of 9–cis retinoic acid, 1992, Genes & Development 6: 329–344.*

Gudas, "Retinoids, Retinoid–responsive Genes, Cell Differentiation, and Cancer"; *Cell Growth & Differentiation*, vol. 3, pp. 655–662, Sep. 1992.

Mokulis, et al., "Screening for Prostate Cancer: Pros, Cons, and Reality"; *Cancer Control*, pp. 15–21, Jan./Feb. 1995.

Merz, et al., "Elevated Transforming Growth Factor–$\beta 1$ and $\beta 3$ mRNA Levels are Associated with ras + myc–Induced Carcinomas in Reconstituted Mouse Prostate: Evidenced for a Paracrine Role during Progression", *Molecular Endocrinology*, vol. 5, No. 4, (1991) pp. 503–513.

Kadmon, et al. Poster Session Abstracts; First Spore Investigators' Meetings, "The Role of Retinoids in Prostate Cancer Chemoprevention" Jul. 18–20, 1993, p. 30.

Slawin, et al., "Dietary Fenretinide, a Synthetic Retinoid, Decreases the Tumor Incidence and the Tumor Mass of ras+myc–induced Carcinomas in the Mouse Prostate Reconstitution Model System", *Cancer Research*, vol. 53, pp. 4461–4465, Oct. 1, 1993.

Thompson, et al., "Transgenic Models for the Study of Prostate Cancer", (Supplement) *Cancer*, vol. 71, No. 3, Feb. 1, 1993, pp. 1165–1171.

Donehower, et al, "Mice deficient for p53 are developmentally normal but susceptible to spontaneous tumours", *Articles*, Nature, vol. 356, Mar. 19, 1992, pp. 215–221.

Thompson, et al., "Loss of p53 function leads to metastasis in ras+myc–initiated mouse prostate cancer", *Oncogene* (1995) vol. 10, pp. 869–879.

Macoska, et al., "Loss of the 17p Chromosomal Region in a Metastatic Carcinoma of the Prostate", *The Journal of Urology*, vol. 147, Apr. 1992, pp. 1142–1146.

Taylor, et al., "Evidence for synergistic interactions between ras, myc and a mutant form of p53 in cellular transformation and tumor dissemination", *Oncogene*, Feb. 10, 1992, pp. 1383–1390.

Hall, et al., "Adenylate Kinase: An Oncodevelopmental Marker in an Animal Model for Human Prostatic Cancer", *Clinical Chemistry*, vol. 31, No. 10, (1985), pp. 1689–1691.

Thompson, et al., Multistage Carcinogenesis Induced by ras and myc Oncogenes in a Reconstituted Organ, *Cell*, vol. 56, pp. 917–930, Mar. 24, 1989.

Slawin, et al., American Urological Association, Inc., Annual Meeting—San Antonio, Oct. 1, 1992, Dietary Retinoids Decrease the Incidence and Increase Lymphocytic Infiltration of ras+myc Induced Carcinomas in the Mouse Prostate Reconstitution Model System.

Thompson, et al., "Transforming Growth Factor $\beta 1$ as a Biomarker for Prostate Cancer", *Journal of Cellular Biochemistry*, Supplement 16H: pp. 54–61 (1992).

(List continued on next page.)

*Primary Examiner*—Deborah Crouch
*Assistant Examiner*—Thaian N. Ton
(74) *Attorney, Agent, or Firm*—Vinson & Elkins L.L.P.

(57) ABSTRACT

The invention relates to methods for the isolation of metastatic sequences and the isolated sequences. Cells from a cell line or an animal tissue are treated to form a cell line predisposed to cancer. Treated cells are implanted in an animal and incubated for a period of time sufficient for the cells to proliferate and develop malignant transplants. RNA from the malignant transplant and the primary tumor are analyzed by differential display polymerase chain reaction. Differentially expressed genes are cloned, reanalyzed, and sequenced. These genes and sequences can be used as probes in the diagnosis of neoplastic disorders, as probes to isolate metastatic sequences and as a therapeutic agent in the treatment of neoplastic disorders. The metastatic sequence may be a dominant metastatic sequence or a recessive metastatic sequence.

14 Claims, 22 Drawing Sheets

OTHER PUBLICATIONS

Thompson, et al., "Genetic Predisposition and Mesenchymal–Epithelial Interactions in ras+myc–Induced Carcinogenesis in Reconstituted Mouse Prostate" *Molecular Carcinogenesis,* vol. 7, pp. 165–179 (1993).

Bookstein et al., "p53 Is Mutated in a Subset of Advanced–Stage Prostate Cancers[1]", *Cancer,* vol. 53, pp. 3369–3373, Jul. 19, 1993.

Carter, et al. "Prediction of Metastatic Potential in an Animal Model of Prostate Cancer: Flow Cytometric Quantification of Cell Surface Charge", *The Journal of Urology,* vol. 142, pp. 1338–1341, Nov. 1989.

Fox, et al., "p53 And c–myc Expression in Stage A1 Prostatic Adenocarcinoma: Useful Prognostic Determinants?", *The Journal of Urology,* vol. 150, pp. 490–494, Aug. 1993.

Einstein, "Hormonal Therapy for Prostate Cancer—When to Use It", *Cancer Control,* Jan./Feb. 1995, pp. 32–36.

Taber's Cyclopedic Medical Dictionary, F.A. David Company, Philadelphia, PA, edited by Vardara et al. (1993).

Welch, et al., "Transforming Growth Factor β Stimulates Mammary Adenocarcinoma Cell Invasion and Metastatic Potential", *Proc. Natl. Acad. Sci. USA,,* vol. 87, pp. 7678–7682. Oct. 1990.

Thompson, et al., "Multistage Carcinogenesis Induced by ras and myc Oncogenes in a Reconstituted Organ", *Cell,* vol. 56,. pp. 917–930. Mar. 24, 1990.

Liang et al., "Differential Display and Cloning of Messenger RN As from Human Breast Cancer versus Mammary Epithelial Cells", *Cancer Research,* 52, pp. 6966–6968. Dec. 15, 1992.

Robson, et al., "Identification of Prostatic Androgen Regulated Genes Using the Differential Display Technique", *Proceedings of the American Association for Cancer Research,* vol. 36, p. 266#1589. Mar., 1995.

Yang, et al., "Association of Caveolin Protein with Prostate Cancer Progression", *Journal of Urology,* vol. 157, No. 4, p. 446, Abstract #1742 (Apr. 1997).

Schlag, P.M., "Früherkennung von Krebs mit Hilfe von molekularbiologischen Markern", *Onkologie,* 18, pp. 2–7, 1995.

Neumann, H.G. "Entstheung und Behandlung von Tumoren, Immunsuppressiva", *Allegmeine und Specielle Pharmakologie and Toxikologie,* Edition 5, 1987.

Liang, Peng, et al. "Differential Display of Eukaryotic Messenger RNA by Means of the Polymerase Chain Reaction", *Science,* vol. 257, pp. 967–971. Aug. 14, 1992.

Wood, David P., Jr., et al. "Sensitivity of Immunohistochemistry and Polymerase Chain Reaction in Detecting Prostate Cancer Cells in Bone Marrow", *The Journal of Histochemistry and Cytochemistry,* vol. 42, No. 4, pp. 505–511. 1994.

Eastham, et al. "Prostate Cancer Gene Therapy: Herpes Simplex Virus Thymidine Kinase Gene Transduction Followed by Ganciclovir in Mouse and Human Prostate Cancer Models", *Human Gene Therapy,* vol. 7, pp. 515–523. Mar. 1, 1996.

Ren, et al. "Identification and characterization of p53 regulared genes in a mouse prostate cancer cell line", AACR Annual Meeting, Mar. 28–Apr. 1, 1998, New Orleans, LA.

Goltsov, et al. "A novel p53–regulated gene encoding a four transmembrane domain protein in mouse prostate cancer cells", AACR Annual Meeting, Apr. 10–14, 1999, Philadelphia, PA.

Ren, et al. "Reduced Lysyl Oxidase in RNA Levels in Experimental and Human Prostate Cancer", *Cancer Research,* vol. 58, pp. 1–6, Mar. 15, 1998.

Nelson, Joel B. "Alternatives to death: Understanding androgen–independent prostate cancer", *Nature Medicine,* vol. 4, No. 9, pp. 1011–1012, Sep. 1998.

Yang, et al. "Elevated Expression of Caveolin Is Associated with Prostate and Breast Cancer", *Clinical Cancer Research,* vol. 4, pp. 1873–1880, Aug., 1998.

Fielding, et al. "Caveolin mRNA levels are up–regulated by free cholesterol and down–regulated by oxysterols in fibroblast monolayers", *Proc. Natl. Acad. Sci. USA,* vol. 94, pp. 3753–3758, Apr., 1997.

Nasu, et al., "Suppression of caveoline expression induces androgen sensitivity in metastatic androgen–insensitive mouse prostate cancer cells", *Nature Medicine,* vol. 4, No. 9, pp. 1062–1064, Sep., 1998.

Bist, et al., "Two sterol regulatory element–like sequences mediate up–regulation of caveolin gene transcription in response to low density lipoprotein free cholesterol", *Proc. Natl. Acad. Sci. USA,* vol. 94, pp. 10693–10698, Sep., 1997.

Li, et al., "Src Tyrosine Kinases, $G_\alpha$ Subunits, and H–Ras Share a Common Membrane–anchored Scaffolding Protein, Caveolin", *The Journal of Biological Chemistry,* vol. 271, No. 46, pp. 29182–29190, 1996.

Tulchinsky, et al., "Transcriptional analysis of the mts1 gene with specific reference to 5' flanking sequences", *Proc. Natl. Acad. Sci. USA,* vol. 89, pp. 9146–9150, Oct., 1992.

Sargiacomo, et al., "Oligomeric structure of caveolin: Implications for caveolae membrane organization", *Proc. Natl. Acad. Sci. USA,* vol. 92, pp. 9407–9411, Sep., 1995.

Eastham, et al., "In Vivo Gene Therapy with p53 or p21 Adenovirus for Prostate Cancer", *Cancer Research,* vol. 55, pp. 5151–5155, Nov. 15, 1995.

Blok, et al., "Isolation of cDNAs That Are Differentially Expressed Between Androgen–Dependent and Androgen–Independent Prostate Carcinoma Cells Uinsg Differential Display PCR", *The Prostate,* vol. 26, pp. 213–224 (1995).

Truong, et al., "Association of Transforming Growth Factor–$\beta_1$ with Prostate Cancer: An Immunohistochemical Study", *Human Pathology,* vol. 24, No. 1, pp. 4–9 (Jan. 1993).

Eastham, et al., "Transforming Growth Factor–$\beta_1$: Comparative Immunohistochemical Localization in Human Primary and Metastatic Prostate Cancer", *Laboratory Investigation,* vol. 73, No. 5, pp. 628–635 (1995).

Aihara, et al., "Frequency of Apoptotic Bodies Positively Correlates with Gleason Grade in Prostate Cancer", *Human Pathology,* vol. 25, No. 8, pp. 797–801 (Aug. 1994).

Aihara, et al., "The Frequency of Apoptosis Correlates with the Prognosis of Gleason Grade 3 Adenocarcinoma of the Prostate", *Cancer,* vol. 75, No. 2, pp. 522–529 (Jan. 15, 1995).

Yang, et al., "Perineural Invasion of Prostate Carcinoma Cells is Associated with Reduced Apoptotic Index", *Cancer,* vol. 78, No. 6, pp. 1267–1271 (Sep. 15, 1996)..

Chamness, et al., "The effect of androgen on nitric oxide synthase in the male reproductive tract of the rat", *Fertility and Sterility,* vol. 63, No. 5, pp. 1101–1107 (May 1995).

Egawa, et al., "Alterations in mRNA Levels for Growth–Related Genes after Transplantation into Castrated Hosts in Oncogene–Induced Clonal Mouse Prostate Carcinoma", *Molecular Carcinogenesis,* 5:52–61, pp. 52–61 (1992).

Stapleton, et al. "Primary Human Prostate Cancer Cells Harboring p53 Mutations are Clonally Expanded in Metastates", *Clinical Cancer Research,* vol. 3, pp. 1389–1397 (Aug. 1997).

Koleske, et al., "Reduction of caveolin and caveolae in oncogenically transformed cells", *Proc. Natl. Acad. Sci. USA,* vol. 92, pp. 1381–1385 (Feb. 1995).

Glenney, John R., "Tyrosine Phosphorylation of a 22–kDa Protein is Correlated with Transformation by Rous Sarcoma Virus", *The Journal of Biological Chemistry,* vol. 264, No. 34, pp. 20163–20166 (Dec. 5, 1989).

Kagan, Herbert M., "Regulation of Matrix Accumulation", Academic Press, Inc., pp. 321–398 (1986).

Kagen, et al., "Properties and Function of Lysyl Oxidase", *Am. J. Respir. Cell Mol. Biol.,* vol. 5, pp. 206–210 (1991).

Anderson, Nature 392/Supp., pp. 25–30.

Thompson, et al., "Caveolin–1, a metastasis–related gene that promotes cell survival in prostate cancer", Apoptosis, vol. 4,, No. 4, pp. 233–237 (1999).

Thompson, et al., "Caveolin–1: a complex and provocative therapeutic target in prostate cancer and potentially other malignancies", Emerging Therapeutic Targets 3(2) pp. 337–346 (1999).

Feres–Filho, et al., "Pre– and Post–translational Regulation of Lysyl Oxidase by Transforming Growth Factor–$\beta$1 in Osteoblastic MC3T3–E1 Cells", *The Journal of Biological Chemistry,* vol. 270, No. 51, pp. 30797–30803 (Dec. 22, 1995).

Shanley, et al., "Transforming growth factor–$\beta_1$ increases lysyl oxidase enzyme activity and mRNA in rat aortic smooth muscle cells", *Journal of Vascular Surgery,* vol. 25, No. 3, pp. 446–452 (Mar. 1997).

Boak, et al., "Regulation of Lysyl Oxidase Expression in Lung Fibroblasts by Transforming Growth Factor–$\beta_1$ and Prostaglandin $E_2$", *American Journal of Respiratory Cell and Molecular Biology,* vol. 11, pp. 751–755 (1994).

Kivirikko, et al., "Posttranslational Modifications of Collagen and Their Alterations in Heritable Diseases", pp. 263–292.

Danks, David M., "Disorders of Copper Transport: Menkes Disease and the Occipital Horn Syndrome", *Connective Tissue and Its Heritable Disorders,* pp. 487–505 (1993).

Kivirikko, Kari L., "Collagens and their Abnormalities in a Wide Spectrum of Diseases", *Annals of Medicine* 25: pp. 113–126 (1993).

Contente, et al. "Expression of Gene rrg Is Associated with Reversion of NIH 3T3 Transformed by LTR–c–H–ras", *Science,* vol. 249, pp. 796–798.

Hajnal, et al., "Up–Regulation of Lysyl Oxidase in Spontaneous Revertants of H–ras–transformed Rat Fibroblasts", pp. 4670–4675.

Fingert, et al., "In vivo model for differentiation therapy of leukemia and solid tumors," National Institutes of Health Publication, 84–2635, Serono Symposia Publications from Rven Press, pp. 277–286 (1984).

Xiong, et al., "Human D–Type Cyclin," Cell, vol. 65: pp. 691–699 (May. 17, 1991).

Manam, et al., "Dose related changes in the profile of ras mutations in chemically induced CD–1 mouse liver tumors," Carcinogenesis, vol. 16(5), pp. 1113–1119 (May 1995).

Blok, et al., "Isolation of cDNA's that are differentially expressed between antrogen–dependent and androgen independent prostate carcinoma cells using diferential display PCT." Prostate, vol. 26(4), pp. 213–224 (Apr. 1995).

Wu, et al., "Identification of a human hepatocellular carcinoma–associated tumor suppressor gene by differential display polymerase chain reaction," Life Sciences, vol. 57(11), pp. 1077–1085 (Nov. 1995).

Schneider, et al., "7,12–Dimethylben[a] anthracene–Induced Mouse Keratinocyte Malignant Transformation Independent of Harvey ras Activation," J. of Investigative Dermatology, vol. 101(4), pp. 595–599 (Oct. 1993).

Tan, et al., "Identification of the Lysyl Oxidase Gene as a Target of the Antioncogenic Transcription Factor, IRF–1, and Its Possible Role in Tumor Suppression", pp. 2417–2421.

Kuivaniemi, et al., "Deficient production of olysyl oxidase in cultures of malignantly transformed human cells", *FEBS Letters,* vol. 195, No. 1,2, pp. 261–264 (Jan. 1986).

Vater, et al., "Native Cross–Links in Collagen Fibrils Induce Resistance to Human Synovial Collagenase", *Biochem J.,* vol. 181, pp. 639–645 (1979).

Hämäläinen, et al., "Quantitative Polymerase Chain Reaction of Lysyl Oxidase mRNA in Malignantly Transformed Human Cell Lines Demonstrates That Their Low Lysyl Oxidase Activity Is Due to Low Quantities of Its mRNA and Low Levels of Transcription of the Respective Gene", *The Journal of Biological Chemistry,* vol. 270, No. 37, pp. 21590–21593 (Sep. 15, 1995).

Peyrol, et al., "Lysyl Oxidase Gene Expression in the Stromal Reaction to in situ and Invasive Ductal Breast Carcinoma", *American Journal of Pathology,* vol. 150, No. 2, pp. 497–507 (Feb. 1997).

Thompson, et al., "Exogenous Leukocyte and Endogenous Elastases Can Mediate Mitogenic Activity in Pulmonary Artery Smooth Muscle Cells by Release of Extracellular Matrix–Bound Basic Fibroblast Growth Factor", *Journal of Cellular Physiology,* vol. 166, pp. 495–505 (1996).

Sehgal, et al., "Transforming Growth Factor $\beta$1 Stimulates Contrasting Responses in Metastatic versue Primary Mouse Prostate Cancer–derived Cell Lines in Vito", *Cancer Research,* vol. 56, pp. 3359–3365 (Jul. 15, 1996).

Shimura, et al. Abstract; American Urological Association 94th Annual Meeting, Dallas, TX, "Reduction in Lysyl Oxidase Expression is an independent Preditor of Recurrence Following Radical Prostatectomy" May 1–6, 1999.

Thompson, "Metastasis–related Genes in Prostate Cancer: The Role of Caveolin–1", *Cancer and Metastasis Reviews,* vol. 17, pp. 439–442, 1999.

Guarini, et al., "Transfer of the Interleukin–2 Gene into Human Cancer Cells Induces Specific Antitumor Recognition and Restores the Expression of CD3/T–Cell Receptor Associated Signal Transduction Molecules," *Blood,* vol. 89, No. 1, pp. 212–218 (Jan. 1, 1997).

Jourdan–Le Saux, et al., "Functional Analysis of the Lysyl Oxidase Promoter in Myofibroblast–Like Clones of 3T6 Fibroblast", Journal of Cellular Biochemistry 64: 328–341, Feb. 1997.

Chen, et al., "Isolation and characterization of the promoter region of human nm23–H1, a metastasis suppressor gene", Abstract 122:2406 (1994).

* cited by examiner

FIGURE 1

```
                9               18                27               36                45
5' TTT AGT CGC  GGT GTC AGC  GCT CGC AGG  ACC ACT CTT  GGC CGC TGC
   --- --- ---  --- --- ---  --- --- ---  --- --- ---  --- --- ---
   Phe Ser Arg  Gly Val Ser  Ala Arg Arg  Thr Thr Leu  Gly Arg Cys
               54               63                72               81                90
   TCC TGC CCG  GCG TTC CTC  CGC TCC GCG  CCC GCC GCC  ACC GAC GAC
   --- --- ---  --- --- ---  --- --- ---  --- --- ---  --- --- ---
   Ser Cys Pro  Ala Phe Leu  Arg Ser Ala  Pro Ala Ala  Thr Asp Asp
               99              108               117              126               135
   ATG CTG CGC  TGC GGC CTG  GCC TGC GAG  CGC TGC AGG  TGG ATC CTG
   --- --- ---  --- --- ---  --- --- ---  --- --- ---  --- --- ---
   Met Leu Arg  Cys Gly Leu  Ala Cys Glu  Arg Cys Arg  Trp Ile Leu
              144              153               162              171               180
   CCC CTG CTG  CTG CTC AGC  GCC ATC GCC  TTC GAC ATC  ATC GCG CTG
   --- --- ---  --- --- ---  --- --- ---  --- --- ---  --- --- ---
   Pro Leu Leu  Leu Leu Ser  Ala Ile Ala  Phe Asp Ile  Ile Ala Leu
              189              198               207              216               225
   GCC GGC CGC  GGC TGG CTG  CAG TCT AGC  AAC CAC ATC  CAG ACA TCG
   --- --- ---  --- --- ---  --- --- ---  --- --- ---  --- --- ---
   Ala Gly Arg  Gly Trp Leu  Gln Ser Ser  Asn His Ile  Gln Thr Ser
              234              243               252              261               270
   TCG CTT TGG  TGG AGG TGT  TTC GAC GAG  GGC GGC GGC  AGC GGC TCC
   --- --- ---  --- --- ---  --- --- ---  --- --- ---  --- --- ---
   Ser Leu Trp  Trp Arg Cys  Phe Asp Glu  Gly Gly Gly  Ser Gly Ser
              279              288               297              306               315
   TAC GAC GAT  GGC TGC CAG  AGC CTC ATG  GAG TAC GCA  TGG GGA CGA
   --- --- ---  --- --- ---  --- --- ---  --- --- ---  --- --- ---
   Tyr Asp Asp  Gly Cys Gln  Ser Leu Met  Glu Tyr Ala  Trp Gly Arg
              324              333               342              351               360
   GCA GCT GCA  GCC ACG CTT  TTC TGT GGC  TTT ATC ATC  CTG TGC ATC
   --- --- ---  --- --- ---  --- --- ---  --- --- ---  --- --- ---
   Ala Ala Ala  Ala Thr Leu  Phe Cys Gly  Phe Ile Ile  Leu Cys Ile
              369              378               387              396               405
   TGC TTC ATT  CTC TCG TTC  TTC GCC CTG  TGT GGA CCC  CAG ATG CTT
   --- --- ---  --- --- ---  --- --- ---  --- --- ---  --- --- ---
   Cys Phe Ile  Leu Ser Phe  Phe Ala Leu  Cys Gly Pro  Gln Met Leu
              414              423               432              441               450
   GTT TTC CTG  AGA GTC ATT  GGA GGC CTC  CTC GCA CTG  GCT GCC ATA
   --- --- ---  --- --- ---  --- --- ---  --- --- ---  --- --- ---
   Val Phe Leu  Arg Val Ile  Gly Gly Leu  Leu Ala Leu  Ala Ala Ile
              459              468               477              486               495
   TTC CAG ATC  ATC TCC CTG  GTA ATC TAC  CCC GTG AAG  TAC ACA CAG
   --- --- ---  --- --- ---  --- --- ---  --- --- ---  --- --- ---
   Phe Gln Ile  Ile Ser Leu  Val Ile Tyr  Pro Val Lys  Tyr Thr Gln
              504              513               522              532               540
   ACC TTC AGG  CTT CAC GAT  AAC CCT GCT  GTT AAT TAC  ATC TAT AAC
   --- --- ---  --- --- ---  --- --- ---  --- --- ---  --- --- ---
   Thr Phe Arg  Leu His Asp  Asn Pro Ala  Val Asn Tyr  Ile Tyr Asn
```

Figure 1 (cont')

```
       549             558             567             576             585
TGG GCC TAT GGC TTC GGA TGG GCG GCC ACC ATC ATC TTG ATT GGT
--- --- --- --- --- --- --- --- --- --- --- --- --- --- ---
Trp Ala Tyr Gly Phe Gly Trp Ala Ala Thr Ile Ile Leu Ile Gly
       594             603             612             621             630
TGT TCC TTC TTC TTC TGC TGC CTC CCC AAC TAC GAG GAT GAC CTT
--- --- --- --- --- --- --- --- --- --- --- --- --- --- ---
Cys Ser Phe Phe Phe Cys Cys Leu Pro Asn Tyr Glu Asp Asp Leu
       639             648             657             666             675
TTG GGG GCC GCC AAG CCC AGG TAC TTC TAT CCC CCA GCC TAA TGT
--- --- --- --- --- --- --- --- --- --- --- --- --- --- ---
Leu Gly Ala Ala Lys Pro Arg Tyr Phe Tyr Pro Pro Ala *** Cys
       684             693             702             711             720
GGG AGG AAG AGC CTG AGA AAA GCC TGC TGC AAG ATG GAT CTG AGG
--- --- --- --- --- --- --- --- --- --- --- --- --- --- ---
Gly Arg Lys Ser Leu Arg Lys Ala Cys Cys Lys Met Asp Leu Arg
       729             738             747             756             765
AGG AAA CTG TTC TCC AAG GCA CAA GGA ACC TAC GTT TGG GCA ATG
--- --- --- --- --- --- --- --- --- --- --- --- --- --- ---
Arg Lys Leu Phe Ser Lys Ala Gln Gly Thr Tyr Val Trp Ala Met
       774             783             792             801             810
TTC ATA TGA TCA GAA ATG CTA GAA TAA ATG CTA AAG AAA ATT CTT
--- --- --- --- --- --- --- --- --- --- --- --- --- --- ---
Phe Ile *** Ser Glu Met Leu Glu *** Met Leu Lys Lys Ile Leu
       819             828             837             846             855
CAT AAT TAG TGT TAA GTT TCA TGT ATG TCG TGT GGA GTT AAA AAG
--- --- --- --- --- --- --- --- --- --- --- --- --- --- ---
His Asn *** Cys *** Val Ser Cys Met Ser Cys Gly Val Lys Lys
       864             873             882             891             900
ACT TGA ATT CTG TTT GCT AAG TAT ATG CTA ATT TTT CCT TAT GTC
--- --- --- --- --- --- --- --- --- --- --- --- --- --- ---
Thr *** Ile Leu Phe Ala Lys Tyr Met Leu Ile Phe Pro Tyr Val
       909             918             927             936             945
AAT TCT ATA CCA TTT AAG CTT CAT TTG TTA AAG AAT ATG CCT GTG
--- --- --- --- --- --- --- --- --- --- --- --- --- --- ---
Asn Ser Ile Pro Phe Lys Leu His Leu Leu Lys Asn Met Pro Val
       954             963             972             981             990
AAA CTT GAT AAG GTA GAA ATG TAG CAG CCT CTC ATT TAA TAA TCT
--- --- --- --- --- --- --- --- --- --- --- --- --- --- ---
Lys Leu Asp Lys Val Glu Met *** Gln Pro Leu Ile *** *** Ser
       999            1008            1017            1026            1035
GAT GGG GCT TCT GTT TTT CCA CAT AGA ATG GGT TGT TTC TGC TAA
--- --- --- --- --- --- --- --- --- --- --- --- --- --- ---
Asp Gly Ala Ser Val Phe Pro His Arg Met Gly Cys Phe Cys ***
```

Figure 1 (cont')

```
        1044            1053            1062            1071            1080
GGG CTA CAG     AGG AGG AAA     GTC ACT GGC     AAA ACT TCC     GTG ACC AAA
--- --- ---     --- --- ---     --- --- ---     --- --- ---     --- --- ---
Gly Leu Gln     Arg Arg Lys     Val Thr Gly     Lys Thr Ser     Val Thr Lys
        1089            1098            1107            1116            1125
TAT CCT GAA     ATT AGT ATT     TTT TTA AAA     AGA CCT TAT     TTT GAG TTT
--- --- ---     --- --- ---     --- --- ---     --- --- ---     --- --- ---
Tyr Pro Glu     Ile Ser Ile     Phe Leu Lys     Arg Pro Tyr     Phe Glu Phe
        1134            1143            1152            1161            1170
TCA GTT ACA     TAA AAA AGC     AGA AGC AGA     TTG GTT TCC     TAA GTG AGC
--- --- ---     --- --- ---     --- --- ---     --- --- ---     --- --- ---
Ser Val Thr     *** Lys Ser     Arg Ser Arg     Leu Val Ser     *** Val Ser
        1179            1188            1197            1206            1215
ATC GTT TGT     GAG AAT TTT     TAG TCA GTG     TTT TGA ACA     ATT ATT GTT
--- --- ---     --- --- ---     --- --- ---     --- --- ---     --- --- ---
Ile Val Cys     Glu Asn Phe     *** Ser Val     Phe *** Thr     Ile Ile Val
        1224            1233            1242            1251            1260
TTT CTA AGC     TTC GTG TTG     ACT TTC TCT     GAT GCG TAG     AAA AGT GTT
--- --- ---     --- --- ---     --- --- ---     --- --- ---     --- --- ---
Phe Leu Ser     Phe Val Leu     Thr Phe Ser     Asp Ala ***     Lys Ser Val
        1279            1278            1287            1296            1305
CTA ACG TAG     CCA AGG TTA     AGC CGC TGT     CAC TAC TGA     AAT GCT AAG
--- --- ---     --- --- ---     --- --- ---     --- --- ---     --- --- ---
Leu Thr ***     Pro Arg Leu     Ser Arg Cys     His Tyr ***     Asn Ala Lys
        1314            1323            1332            1341            1350
AAT TTT CCT     CTT TTC CCG     TAG TGT AGA     GGG GTA GGG     TGT GGG AAG
--- --- ---     --- --- ---     --- --- ---     --- --- ---     --- --- ---
Asn Phe Pro     Leu Phe Pro     *** Cys Arg     Gly Val Gly     Cys Gly Lys
        1359            1368            1377            1386            1395
AAG CCG TGT     TAG CAC ATC     TGT AGT ATT     CTG TGT GTA     TGC TTA GAA
--- --- ---     --- --- ---     --- --- ---     --- --- ---     --- --- ---
Lys Pro Cys     *** His Ile     Cys Ser Ile     Leu Cys Val     Cys Leu Glu
        1404            1413            1422            1431            1440
CCA GCG TAG     ACC GGA TGG     GAG GAT GGA     CTA GGC CTA     ATC CCT CCC
--- --- ---     --- --- ---     --- --- ---     --- --- ---     --- --- ---
Pro Ala ***     Thr Gly Trp     Glu Asp Gly     Leu Gly Leu     Ile Pro Pro
        1449            1458            1467            1476            1485
AAC TGG TGG     ATG TGA AGA     GGT CAG GTA     GGA AGG CAC     AGG AGG GTC
--- --- ---     --- --- ---     --- --- ---     --- --- ---     --- --- ---
Asn Trp Trp     Met *** Arg     Gly Gln Val     Gly Arg His     Arg Arg Val
        1494            1503            1512            1521            1530
ACC ACT GTC     ACA GCA GTG     CCA TGC AGA     CAT CCT AGG     AGA AGA CAT
--- --- ---     --- --- ---     --- --- ---     --- --- ---     --- --- ---
Thr Thr Val     Thr Ala Val     Pro Cys Arg     His Pro Arg     Arg Arg His
```

Figure 1 (cont')

```
        1539            1548            1557            1566            1575
GGC AGT GTT     TCT TCT CAG     TGC TTC TTC     CCT TAA CTG     AGC TCT GCT
--- --- ---     --- --- ---     --- --- ---     --- --- ---     --- --- ---
Gly Ser Val     Ser Ser Gln     Cys Phe Phe     Pro *** Leu     Ser Ser Ala
        1584            1593            1602            1611            1620
CAC AGA CAG     CTA GAA TAG     ATT TTA ACT     GTA ACA GAA     ACC TAA ATG
--- --- ---     --- --- ---     --- --- ---     --- --- ---     --- --- ---
His Arg Gln     Leu Glu ***     Ile Leu Thr     Val Thr Glu     Thr *** Met
        1629            1638            1647            1656            1665
TAA TTA AAA     CCT GGT CTT     CCT TGG TAA     GCA GAC TTA     AAA TAT CTG
--- --- ---     --- --- ---     --- --- ---     --- --- ---     --- --- ---
*** Leu Lys     Pro Gly Leu     Pro Trp ***     Ala Asp Leu     Lys Tyr Leu
        1674            1683            1692            1701            1710
TAT AGT ACA     TGC AAG TGG     AAA ATT TGG     GAA TGC GTG     TCT CTG AAT
--- --- ---     --- --- ---     --- --- ---     --- --- ---     --- --- ---
Tyr Ser Thr     Cys Lys Trp     Lys Ile Trp     Glu Cys Val     Ser Leu Asn
        1719            1728            1737            1746            1755
ACA TAC CGG     AAG GGC TAC     TAT TAC CTT     TTC CTT ACC     ATT TAT ACT
--- --- ---     --- --- ---     --- --- ---     --- --- ---     --- --- ---
Thr Tyr Arg     Lys Gly Tyr     Tyr Tyr Leu     Phe Leu Thr     Ile Tyr Thr
        1764            1773            1782            1791            1800
TAC CTA ATG     GAA ACG AGC     TTG TTT TAA     CTA TCA GAA     CAC TAT TTT
--- --- ---     --- --- ---     --- --- ---     --- --- ---     --- --- ---
Tyr Leu Met     Glu Thr Ser     Leu Phe ***     Leu Ser Glu     His Tyr Phe
        1809            1818            1827            1836            1845
GTA AGG TGC     TGC AAA GAC     AGT TGA AGT     TTT CAT TAC     CAA CTT CCC
--- --- ---     --- --- ---     --- --- ---     --- --- ---     --- --- ---
Val Arg Cys     Cys Lys Asp     Ser *** Ser     Phe His Tyr     Gln Leu Pro
        1854            1863
CAA TAA ACC     AGG TGT TCA     AAA AAA A 3'
--- --- ---     --- --- ---     --- --- ---
Gln *** Thr     Arg Cys Ser     Lys Lys
```

FIGURE 2

| Clone # | seq. length(nt) | primer # | screen type (p53/TGF-beta/Met) |
|---|---|---|---|
| Cl1-2 | 155 | P2 | Met |
| Cl2-2 | 275 | P2 | Met |
| Cl2-3 | 194 | P2 | Met |
| Cl2-4 | 230 | P2 | Met |
| Cl3-1 | 241 | P3 | Met |
| Cl4-1 | 156 | P3 | Met |
| Cl5A-4 | 233 | P2 | Met |
| Cl6-2 | 287 | P1 | Met |
| Cl7-4 | 262 | P1 | Met |
| Cl8-2 | 284 | P1 | Met |
| Cl9-1 | 278 | P1 | Met |
| Cl10-3 | 268 | P1 | Met |
| Cl11A-5 | 302 | P2 | Met |
| Cl11C-2 | 314 | P2 | Met |
| Cl12-1 | 283 | P2 | Met |
| Cl13-1 | 297 | P2 | Met |
| Cl14-4 | 242 | P2 | Met |
| Cl15-1 | 236 | P2 | Met |
| Cl16-3 | 272 | P2 | Met |
| Cl17-1 | 272 | P2 | Met |
| Cl18-3 | 196 | P2 | Met |
| Cl20-4 | 187 | P1 | Met |
| Cl22-2 | 197 | P2 | Met |
| Cl23A-1 | 200 | P2 | Met |
| Cl23BC-6 | 256 | P2 | Met |
| Cl24-3 | 285 | P5 | Met |
| Cl25-2 | 231 | P5 | Met |
| Cl26A-4 | 300 | P2 | Met |
| Cl26BC-6 | 254 | P2 | Met |
| Cl27A-1 | 331 | P3 | Met |
| Cl27B-1 | 241 | P3 | Met |
| Cl27C-2 | 256 | P3 | Met |
| Cl29#3 | 335 | P5 | Met |
| Cl40-2 | 243 | P9 | Met |
| Cl43-5 | 404 | P6 | Met |
| Cl48-2 | 167 | P7 | Met |
| Cl54-4 | 212 | P8 | Met |
| Cl56-4 | 212 | P9 | Met |
| Cl60-2 | 214 | P10 | Met |
| Cl63-4 | 341 | P10 | Met |
| Cl70-2 | 303 | P11 | Met |
| Cl71-2 | 234 | P11 | Met |

Figure 2 (cont')

| Clone # | seq. length(nt) | primer # | screen type (p53/TGF-beta/Met) |
|---|---|---|---|
| Cl72-1 | 343 | P11 | Met |
| Cl72-2 | 346 | P11 | Met |
| Cl74-2 | 315 | P11 | Met |
| Cl79A-3 | 204 | P12 | Met |
| Cl80-3 | 200 | P11 | Met |
| P2-20 Cl1 | 371 | P2 | Met |
| P2-26 Cl1 | 319 | P2 | Met |
| P9-22 Cl9 | 348 | P9 | Met |
| P9-25 Cl3 | 351 | P9 | Met |
| P15-11 Cl2 | 390 | P15 | Met |
| P17-6 Cl10 | 298+337 | P17 | Met |
| P18-17 Cl2 | 343 | P18 | Met |
| P19-5 Cl3 | 337 | P19 | Met |
| P19-6 Cl2 | 322+262 | P19 | Met |
| P20-35 Cl9 | 482 | P20 | Met |
| P21-11 Cl2 | 368 | P21 | Met |
| P21-17 Cl9 | 287 | P21 | Met |
| P21-9 Cl6 | 332 | P21 | Met |
| P21-24 Cl5 | 380 | P21 | Met |
| P21-25 Cl2 | 353 | P21 | Met |
| P21-6 Cl3 | 331 | P21 | Met |
| P22-5 Cl3 | 359 | P22 | Met |
| P22-6 Cl14 | 317 | P22 | Met |
| P22-9 Cl3 | 317 | P22 | Met |
| P24-10 Cl3 | 287 | P24 | Met |
| P24-6 Cl3 | 311 | P24 | Met |
| P24-9 Cl10 | 326 | P24 | Met |
| P24-11 Cl3 | 350 | P24 | Met |
| P25-1 Cl3 | 352 | P25 | Met |
| P25-9 Cl8 | 317 | P25 | Met |
| P25-7 Cl3 | 247 | P25 | Met |
| MP37-4 Cl2 | 367 | P37 | Met |
| MP37-5 Cl7 | 331 | P37 | Met |
| MP42-6 Cl7 | 340 | P42 | Met |
| MP43-10 Cl8 | 365 | P43 | Met |
| MP44-6 Cl4 | 343 | P44 | Met |
| MP45-10 Cl10 | 315 | P45 | Met |
| P11-2 Cl5 | 318 | P11 | TGF-beta |
| P11-14 Cl1 | same as P11-2 Cl5 | P11 | TGF-beta |
| P17-3 Cl8 | 373 | P11 | TGF-beta |
| P18-12 Cl3 | 333 | P18 | TGF-beta |
| P20-3 Cl8 | 295 | P20 | TGF-beta |
| P20-23 Cl9 | 227 | P20 | TGF-beta |
| P19-1 Cl3 | 296 | P19 | TGF-beta |

Figure 2 (cont')

| Clone # | seq. length(nt) | primer # | screen type (p53/TGF-beta/Met) |
|---|---|---|---|
| P1-8 Cl10 | 383 | P1 | p53 |
| P1-9 Cl10 | 256 | P1 | p53 |
| P2-13 Cl4 | 145 | P2 | p53 |
| P7-4 Cl1 | 340 | P7 | p53 |
| P9-17 Cl9 | 252 | P9 | p53 |
| P9-20 Cl3 | 304 | P9 | p53 |
| P9-23 Cl6 | 102 | P9 | p53 |
| P11-23 Cl2 | 400 | P11 | p53 |
| P15-14 Cl5 | 349 | P15 | p53 |
| P15-9 Cl1 | 374+292 | P15 | p53 |
| P18-23 Cl10 | 291 | P18 | p53 |
| P24-23 Cl10 | 377 | P24 | p53 |
| P30-2 Cl4 | 189 | P30 | p53 |
| P30-8 Cl6 | 263 | P30 | p53 |
| P32-1 Cl6 | 321 | P32 | p53 |
| P32-12 Cl2 | 313 | P32 | p53 |
| P33-14 Cl2 | 267 | P33 | p53 |
| P40-12 Cl9 | 358 | P40 | p53 |
| P45-2 Cl9 | 305 | P45 | p53 |
| P45-5 Cl4 | 338 | P45 | p53 |
| P64-5 Cl1 | 354 | P64 | p53 |
| P66-2 Cl10 | 265 | P66 | p53 |
| P66-1 Cl1 | 240 | P66 | p53 |
| P67-8 | | P67 | p53 |
| P72-5 Cl8(p53) | 306 | P72 | p53 |
| P72-7 Cl3(p53) | 303 | P72 | p53 |
| P74-6 Cl2 | | P74 | p53 |
| P99-2 Cl9 | 324 | P99 | p53 |
| P136-3 Cl7 | 355 | P136 | p53 |
| P142-1 Cl10 | 373 | P142 | p53 |
| P144-3 Cl7 | 696 | P144 | p53 |
| P157-1 Cl8 | 217 | P157 | p53 |
| P157-4 Cl9 | 433 | P157 | p53 |
| P159-1 Cl8 | 148 | P159 | p53 |
| P157-3A Cl9 | 440 | P157 | p53 |
| Cl29 N3 (nmb) | 2295 | P5 | Met |
| Cl54A DN5 | 5300 | P8 | Met |
| P20-35 CN5 | 6571 | P20 | Met |
| P24-11 BN2 | 4160 | P24 | Met |
| P24-11 BN14 | 4345 | P24 | Met |
| P7-4 AN2 | 3682 | P7 | p53 |
| P99-2 NM13-2 | 1870 | P99 | p53 |
| P99-2 DN9-1 | 1870 | P99 | p53 |
| P144-3 AN42-3 | 1008 | P144 | p53 |

Figure 2 (cont')

| Clone # | seq. length(nt) | primer # | screen type (p53/TGF-beta/Met) |
|---|---|---|---|
| P157-3ADN10 | 2586 | P157 | p53 |

FIGURE 3

| Clone # | cDNA from Cell Lines | DD Primer | PCR Size (nt) | Mouse Homology | Human Homology | Northern big blot # | Regulation Type |
|---|---|---|---|---|---|---|---|
| Cl 3#1 Cl 4#1 (same frag & orientation) | 151-2 LMB | P3 | | Tyrosine Kinase? Vip2 | Caveolin (70%) | N123 148-1 up 151-1 up 151-2 up | up |
| Cl 5A#4 | 148-1 PA | P2 | | Thrombo-spondin 100% | | N124 148-1 down 151-1 down 151-2 up | down |
| Cl 25#3 | 151-2 LMA | P5 | | | 53BP2 P53-binding protein (53.3%) | 148-1 down 151-1 down 151-2 up | down |
| Cl 29#3 Cl 28#1 (same frag; different orientation) | 148-1 LMD | P5 | 400 400 | | TGF-Beta 2 (53.0%) Kvi-1 | N119 148-1 up 151-1 up 151-2 up | up |
| Cl 54A#2 | 148-1 PA | P8 | | Musculus receptor tyrosin kinase (53.1%) R.norvegicus mRNA for cyclin G (52.9%) | Proto-oncogene tyrosine-protein kinase gene (47.2%) | N126 148-1 down (weak) 151-1 down (weak) 151-2 up (weak) | down |

Figure 3 (cont')

| Clone # | cDNA from Cell Lines | DD Primer | PCR Size (nt) | Mouse Homology | Human Homology | Northern big blot # | Regulation Type |
|---|---|---|---|---|---|---|---|
| Cl 63#4 | 151-2 LMA | P10 | | | Y316 gene (53.8%) 1AC gene (53.8%) Rb susceptibility gene (50%) | N127 148-1 up 151-1 down 151-2 up | up |
| Cl 74#2 | 151-2 LMA | P11#3 | | 86.8% serum & glucocorticoid regulated kinase (sgk) | | N120 148-1 up 151-1 down 151-2 up | |
| Cl 75#1 | 151-2 LMA | P11#10 | | 87% match sgk | | | up |
| Cl 78B#4 match the same gene but diff. frag. | 148-1 LMD | P12 | | 92.2% match sgk | protein kinase CL (57%) | | |
| Cl72#1 | 148-1 PA | P11 | | MIPP, myosin heavy chain mRNA (50.2%) | CDC25 (48.4%) | N131 148-1 down 151-1 down 151-2 down | |

FIGURE 4

| DD-PCR primer and PCR size (nt) | Mouse homology (%nt) | Human homology (%nt) | Northern (P-MT) (screen 1) | Northern-cloned DNA (P-MT) (screen 2) |
|---|---|---|---|---|
| P17-6 cl10 (1100) | muscle nicotinic acetylcholine receptor alpha (54.3%) | | no | 151-1LM1 up, 151-1 LMA down |
| P19-6 cl2 (500) | | lymphocyte IgE receptor (52.6%) | no | 151-2LMA down, down |
| P21-6 cl3 (450) | histon H2b (94.2%) | | 151-1LM1 down, down | 151-1LM1 down, down |
| P21-9 cl6 (600) | Rattus norvegicus thiol-specific antioxidant mRNA (94.4%) | | 151-1LM1 down, down 151-2LMA up, up | 151-1LM1 down, down 151-2LMA up, up |
| P21-17 cl9 (1000) | Mus musculus putative protein tyrosin phosphatase mRNA (98.3%) | | 148-1LMD up, up 151-1LM1 up, up | 148-1LMD up, up 151-1LM1 up, up |
| P22-5 cl3 (600) | Rat dihydropyridine-sensitive L-type calcium channel alpha-2 subunit gene (92.5%) | | 148-1LMD up, up | 148-1LMD up, up |
| P22-6 cl4 (600) | same as P22-5 cl3 | | 148-1LMD up 151-1LM1 up | 148-1LMD up, up |
| P22-9 cl3 (800) | Rat kidney Zn-peptidase aminopeptidase N mRNA (90.5%) | | 148-1LMD up, up, up | 148-1LMD up, up, up |
| P24-6 cl3 (550) | | ubiquitin carrier protein (E2-EPF) mRNA (53.3%) | 151-1LM1 down 151-2LMA up 151-2LMB up | 151-2LMA up |

Figure 4 (cont')

| DD-PCR primer and PCR size (nt) | Mouse homology (%nt) | Human homology (%nt) | Northern (P-MT) (screen 1) | Northern-cloned DNA (P-MT) (screen 2) |
|---|---|---|---|---|
| P24-cl10 (1000) | Rattus norvegius calpain II 80 kDa subunit mRNA (78.1%) | | 151-1LM1 up, up, up 151-2MMA up, up, up | 151-1 LM1 up, up |
| P24-11 cl3 (1500) | rat C2A gene for prostatic binding protein (PBP) (47.9%), mouse interleukin 1-beta (IL-1-beta)mRNA (51.8%) | cytosolic phospholipase A2 gene (51.2%), human growth hormone (GH-1 and GH-2) and chorionic somatomammo tropin (cs-1, CS-2 and CS-5) genes (51.7%) | 151-1LM1 up, up 151-2MMA up, up | 151-2MMA up |
| P25-5 cl8 | rat IGFBP-3 (86.4%) | | | 151-1 LM1 down, down, down 151-2 LMA up, up, up |
| P20-29 cl2 | | human endothelial differentiation protein gene mRNA (51.4%) | | 148-1 LMD up, up, up 151-2 MMA down, down, down |
| P21-3 cl10 | mouse topoisomerase I mRNA (50.5%) | | | 151-2 LMA up, up |

Figure 4 (cont')

| DD-PCR primer and PCR size (nt) | Mouse homology (%nt) | Human homology (%nt) | Northern (P-MT) (screen 1) | Northern-cloned DNA (P-MT) (screen 2) |
|---|---|---|---|---|
| P24-cl10 (1000) | Rattus norvegius calpain II 80 kDa subunit mRNA (78.1%) | | 151-1LM1 up, up, up 151-2MMA up, up, up | 151-1 LM1 up, up |
| P24-11 cl3 (1500) | rat C2A gene for prostatic binding protein (PBP) (47.9%), mouse interleukin 1-beta (IL-1-beta)mRNA (51.8%) | cytosolic phospholipase A2 gene (51.2%), human growth hormone (GH-1 and GH-2) and chorionic somatomammo tropin (cs-1, CS-2 and CS-5) genes (51.7%) | 151-1LM1 up, up 151-2MMA up, up | 151-2MMA up |
| P25-5 cl8 | rat IGFBP-3 (86.4%) | | | 151-1 LM1 down, down, down 151-2 LMA up, up, up |
| P20-29 cl2 | | human endothelial differentiation protein gene mRNA (51.4%) | | 148-1 LMD up, up, up 151-2 MMA down, down, down |
| P21-3 cl10 | mouse topoisomerase I mRNA (50.5%) | | | 151-2 LMA up, up |

FIGURE 5

| DD-PCR primer and PCR size (nt) | Mouse (rodent) homology (%) | Human homology (%) | screen 1 (P-MT) | screen 2 (P-MT) |
|---|---|---|---|---|
| P2-20 cl1 (800) | rat pancreatic cationic trypsinogen mRNA (46.6%) | cholesterol 7-alpha hydroxylase (58.5%) | 148-1 LMD up, up | 148-1LMD up, up |
| P2-26 cl1 (900) | M.musculus mRNA for integrin alpha6 subunit (98.9%) | | 148-1LMD up, up | 148-1LMD up, up, up |
| P9-22 cl9 (850) | | Human novel protein AHNAK mRNA (50%) | 148-1LMD up, up | 148-1LMD up, up |
| P9-25 cl3 (850) | | carboxypeptidase M, 3' end (80.2%) | 148-1LMD up, up | 148-1LMD up, up |
| P11-14 cl1 (350) | lysyl oxidase mRNA (98.4%) | | 148-1LMD down, down | 148-1LMD down, down |
| P20-35 cl9 (500) | rat insulin-like growth factor 1 gene (45.8%) | H. Sapiens HK2 mRNA for hexokinase II (52.2%) | 148-1LMD up, up | 148-1LMD up, up |
| P21-24 cl5 (350) | Mus musculus ELF-1 precursor mRNA (47.9%) | cAMP responsive element binding protein beta subunit mRNA (48.6%) | 148-1LMD up, up | 148-1LMD up, up, up |
| P21-25 cl2 (370) | | plasminogen activator inhibitor-1 gene exons 2-9 (46.7%) | 148-1LMD up | 148-1LMD up |

Figure 5 (cont')

| DD-PCR primer and PCR size (nt) | Mouse (rodent) homology (%) | Human homology (%) | screen 1 (P-MT) | screen 2 (P-MT) |
|---|---|---|---|---|
| P15-11 cl2 (700) | murine serum amyloid A-1 (SAA-1) gene (46.7%), cDNA encoding mucin-like protein (49.6%) | Human mRNA for type 2 inositol 1, 4, 5-trisphosphate receptor (46.5%), H. sapiens mRNA for HLA-DR associated protein II (46.5%) | 148-1LMD up, up, up | 148-1LMD up, up |

FIGURE 6

| DD-PCR primer and PCR size (nt) | Mouse (rodent) homology (%nt) | Human homology (% nt) | screen 1 P53 stimulatory response (12h. or 24h.) | screen 2 cloned DNA |
|---|---|---|---|---|
| P1-8 cl10 (1000) | | dystrophin gene (50.4%) | P53(+)24 down, down | P53(+)24 down, down |
| P1-9 cl10 (500) | M. musculus mRNA for cyclin G (96.5%) | | P53(+)12 up, up P53(+)24 up, up, up | P53(+)12 up, up, up P53(+)24 up, up, up |
| P7-4 cl1 (600) | rattus norvegicus sgk mRNA (51.3%), rat lung derived L01 C-ros-1 proto oncogene mRNA (48.4%) | nitric oxide synthase (47.1%) | 148-1LMD down P53(+)12 up, up P53(+)24 up, up, up | P53(+)12 up P53(+)24 up, up |
| P9-17 cl9 (500) | rat mRNA for cyclin D1 (79.1%) | | P53(+)24 up | P53(+)24 up |
| P9-20 cl3 (850) | | H. sapiens LDLC mRNA (51.8%) dystrophin gene (49.8%) | P53(+)12 down P53(+)24 down, down | P53(+)12 down, down P53(+)24 down |
| P11-23-cl2 (800) | syrian hamster gene for cytochrome P-4 (52.5%), rat carbohydrate binding receptor gene (50.6%) | | P53(+)24 up, up | P53(+)24 up |
| P15-9 cl1 (600) | mouse (clone BALB11N) mRNA (47.2%) | PTGS2 gene for prostaglandin endoperoxide synthase-2 (46.6%) | P53(+)24 down | P53(+)12 down, down P53(+)24 down, down |

Figure 6 (cont')

| DD-PCR primer and PCR size (nt) | Mouse (rodent) homology (%nt) | Human homology (% nt) | screen 1 P53 stimulatory response (12h. or 24h.) | screen 2 cloned DNA |
|---|---|---|---|---|
| P15-14 cl5 (500) | Mus musculus protein synthesis elongation factor Tu (eEF-Tu, eEf-1-alpha) mRNA (97.2%) | | P53(+)12 up P53(+)24 up | P53(+)24 up |
| P18-23 cl10 (500) | mouse ferritin heavy chain (MFH) mRNA (99.7%) | | 148-1LMD down P53(+)12 down P53(+)24 down | 148-1LMD down P53(+)12 down P53(+)24 down |
| P24-23 cl10 (550) | Mus musculus BALB/c T-cell antigen 4-1BB gene (50.9%) | human mRNA for cripto protein (47.1%), human int-2 proto-oncogene (49.9%) | 148-1LMD down P53(+)12 down | P53(+)12 down |
| P2-7 (cl18#3) | rattus norvegicus glypican (93.4%) | | | 148-1LMD down P53(+)12 down |
| DN5 (Cl54A#2) | Musculus receptor tyrosin kinase (53.1%) R.norvegicus mRNA for cyclin G (52.9%) | Proto-oncogene tryosine-protein kinase gene (47.2%) | | P53(+) down, down |
| P30-2 Cl4 | | | | P53(+)12 down P53(+)24 down |
| P9-23 Cl6 | | | | P53(−)12 down P53(−)24 down |

Figure 6 (cont')

| DD-PCR primer and PCR size (nt) | Mouse (rodent) homology (%nt) | Human homology (% nt) | screen 1 P53 stimulatory response (12h. or 24h.) | screen 2 cloned DNA |
|---|---|---|---|---|
| TGF-beta1 | | | | P53(+)12 down P53(+)24 down |

FIGURE 7

| DD-PCR Primer and PCR size (nt) | Mouse homology (%nt) | Human homology (% nt) | TGF-beta stimulatory response (12hr) | Cell line |
|---|---|---|---|---|
| P11-2 cl5 (310) | lysyl oxidase (100%) | | T6: up, up, up | N132: 148-1 LMD, 151-1 LM 1 down, 151-2 LMB, 151-2 LMC up |
| P20-23 cl9 (850) | actin binding protein (100%) | | T8: up, up | N142: 148-1 LMD, 151-2 LMA, LMB, MMA up, 151-1 LM1 unchanged |
| Cl29-3 (P5) (335) | | nmb (79.8%) | T6: down, down | N119: 148-1 LMD, 151-1 LM1, 151-2 LMA, LMB, LMC, MMA up |
| P17-3 cl8 (1000) | ubiquitin activating enzyme E1 (100%) | | up | N142: 151-2 LMA down |
| P20-3 cl3 (400) | | alpha actinin 3 mRNA (77.5%) | T6: up, up | N133 (11-20) |
| P18-12 cl3 (1000) | rat mRNA for P34 protein (89.6%) | | T9 T(+)12 up, up T(+)24 down, down, down | N120 |
| P25-7 cl3 (1000) | M. musculus mRNA for P19-protein tyrosine phosphatase (100%) | | T9: up | 148-1LMD up |
| P19-1 cl3 (310) | | polymorphic loci in Xq28 (30%) | T8, T13: up | |

FIGURE 8

| DD-PCR primer and PCR size (nt) | mouse (rodent) homology (%nt) | human homology (%nt) | screen 1 (uncloned probed) | screen 2 (cloned probed) | screen 3A | positive plaque No. in library (148-1 LMD) screening (from 12 membranes) |
|---|---|---|---|---|---|---|
| P7-4 cl1 (600) | rattus norvegicus sgk mRNA (51.3%), rat lung derived L01 C-ros-1 proto-oncogene mRNA (48.4%) | nitric oxide synthase (47.1%) | 148-1LMD down P53(+)12 up, up P53(+)24 up, up, up | P53(+)12 up P53(+)24 up, up | 148-1 LMD no difference 151-1 LM1 up 151-2 LMC, MMA down | 12 |
| P20-35 cl9 (500) | rat insulin-like growth factor 1 gene (45.8%) | H. sapiens HK2 mRNA for hexokinase II (52.2%) | 148-1LMD up, up | 148-1LMD up, up | 148-1 LMD up, up, up 151-1 LM1 up 151-2 LMA up, up, up, up 151-2 LMB up, up, up 151-2 LMC, MMA up, up | 8 |

Figure 8 (cont')

| DD-PCR primer and PCR size (nt) | mouse (rodent) homology (%nt) | human homology (%nt) | screen 1 (uncloned probed) | screen 2 (cloned probed) | screen 3A | positive plaque No. in library (148-1 LMD) screening (from 12 membranes) |
|---|---|---|---|---|---|---|
| P24-11 cl3 (1500) | rat C2A gene for prostatic binding protein (PBP) (47.9%), mouse interleukin 1-beta (IL-1-beta) mRNA (51.8%) | cytosolic phospho-lipase A2 gene (51.2%), human growth hormone (GH-1 and GH-2) and chorionic somatomam motropin (CS-1, CS-2 and CS-5) | 151-1LM1 up, up 151-2MMA up, up | 151-2MMA up | 148-1LMD up, up 151-1 LM1 no difference 151-2 LMA, LMB up, up 151-2 LMC up 151-2 MMA up, up, up | 147 |
| Cl 54A#2 | M. musculus mRNA for cyclic nucleotide phosphodie sterase (99.8%) | Proto-oncogene tyrosine-protein kinase gene (47.2%) | | | 148-1 LMD down, down 151-1 LM1 down, down 151-2 LMA, LMB, LMC, MMA up, up | 26 |

FIGURE 9

| DD-PCR Primer | mouse homology | human homology | TGFβ Stimulatory response (12 hrs) | metastasis v. primary expression as determined by RNA blot. |
|---|---|---|---|---|
| $P_{11}$-2cl5 | lysyl oxidase (100%) | | +++ | ++ |
| $P_{20}$-2cl9 | actin binding protein (100%) | | ++ | ++ |
| cl29#3 | | nmb (80%) | -- | ++ |
| $P_{17-3}$cl8 | ubiquitin activating enzyme E1 (100%) | | + | -- |
| $P_{20-3}$ | | α actinin 3 mRNA (77.5%) | ++ | |
| $P_{18}$-12cl3 | Rat mRNA for p34 protein (89.6%) | | ++ | |

SEQUENCE LISTING

<160> NUMBER OF SEQ ID NOS: 27

<210> SEQ ID NO 1
<211> LENGTH: 1870
<212> TYPE: DNA
<213> ORGANISM: Mus sp.
<220> FEATURE:
<221> NAME/KEY: CDS
<222> LOCATION: (1)..(1869)

<400> SEQUENCE: 1

```
ttt agt cgc ggt gtc agc gct cgc agg acc act ctt ggc cgc tgc tcc       48
Phe Ser Arg Gly Val Ser Ala Arg Arg Thr Thr Leu Gly Arg Cys Ser
 1               5                  10                  15 tgc ccg gcg ttc ctc cgc tcc gcg ccc gcc gcc acc gac gac atg ctg       96
Cys Pro Ala Phe Leu Arg Ser Ala Pro Ala Ala Thr Asp Asp Met Leu
                20                  25                  30 cgc tgc ggc ctg gcc tgc gag cgc tgc agg tgg atc ctg ccc ctg ctg      144
Arg Cys Gly Leu Ala Cys Glu Arg Cys Arg Trp Ile Leu Pro Leu Leu
            35                  40                  45 ctg ctc agc gcc atc gcc ttc gac atc atc gcg ctg gcc ggc cgc ggc      192
Leu Leu Ser Ala Ile Ala Phe Asp Ile Ile Ala Leu Ala Gly Arg Gly
        50                  55                  60 tgg ctg cag tct agc aac cac atc cag aca tcg tcg ctt tgg tgg agg      240
Trp Leu Gln Ser Ser Asn His Ile Gln Thr Ser Ser Leu Trp Trp Arg
 65                  70                  75                  80 tgt ttc gac gag ggc ggc ggc agc ggc tcc tac gac gat ggc tgc cag      288
Cys Phe Asp Glu Gly Gly Gly Ser Gly Ser Tyr Asp Asp Gly Cys Gln
                85                  90                  95 agc ctc atg gag tac gca tgg gga cga gca gct gca gcc acg ctt ttc      336
Ser Leu Met Glu Tyr Ala Trp Gly Arg Ala Ala Ala Ala Thr Leu Phe
               100                 105                 110 tgt ggc ttt atc atc ctg tgc atc tgc ttc att ctc tcg ttc ttc gcc      384
Cys Gly Phe Ile Ile Leu Cys Ile Cys Phe Ile Leu Ser Phe Phe Ala
           115                 120                 125 ctg tgt gga ccc cag atg ctt gtt ttc ctg aga gtc att gga ggc ctc      432
Leu Cys Gly Pro Gln Met Leu Val Phe Leu Arg Val Ile Gly Gly Leu
       130                 135                 140 ctc gca ctg gct gcc ata ttc cag atc atc tcc ctg gta atc tac ccc      480
Leu Ala Leu Ala Ala Ile Phe Gln Ile Ile Ser Leu Val Ile Tyr Pro
```

-continued

| | |
|---|---|
| gtg aag tac aca cag acc ttc agg ctt cac gat aac cct gct gtt aat<br>Val Lys Tyr Thr Gln Thr Phe Arg Leu His Asp Asn Pro Ala Val Asn<br>165                      170                    175 | 528 |
| tac atc tat aac tgg gcc tat ggc ttc gga tgg gcg gcc acc atc atc<br>Tyr Ile Tyr Asn Trp Ala Tyr Gly Phe Gly Trp Ala Ala Thr Ile Ile<br>180                      185                    190 | 576 |
| ttg att ggt tgt tcc ttc ttc ttc tgc tgc ctc ccc aac tac gag gat<br>Leu Ile Gly Cys Ser Phe Phe Phe Cys Cys Leu Pro Asn Tyr Glu Asp<br>195                      200                    205 | 624 |
| gac ctt ttg ggg gcc gcc aag ccc agg tac ttc tat ccc cca gcc taa<br>Asp Leu Leu Gly Ala Ala Lys Pro Arg Tyr Phe Tyr Pro Pro Ala<br>210                      215                    220 | 672 |
| tgt ggg agg aag agc ctg aga aaa gcc tgc tgc aag atg gat ctg agg<br>Cys Gly Arg Lys Ser Leu Arg Lys Ala Cys Cys Lys Met Asp Leu Arg<br>225                      230                    235                    240 | 720 |
| agg aaa ctg ttc tcc aag gca caa gga acc tac gtt tgg gca atg ttc<br>Arg Lys Leu Phe Ser Lys Ala Gln Gly Thr Tyr Val Trp Ala Met Phe<br>245                      250                    255 | 768 |
| ata tga tca gaa atg cta gaa taa atg cta aag aaa att ctt cat aat<br>Ile     Ser Glu Met Leu Glu     Met Leu Lys Lys Ile Leu His Asn<br>260                      265                    270 | 816 |
| tag tgt taa gtt tca tgt atg tcg tgt gga gtt aaa aag act tga att<br>    Cys     Val Ser Cys Met Ser Cys Gly Val Lys Lys Thr     Ile<br>275                      280                    285 | 864 |
| ctg ttt gct aag tat atg cta att ttt cct tat gtc aat tct ata cca<br>Leu Phe Ala Lys Tyr Met Leu Ile Phe Pro Tyr Val Asn Ser Ile Pro<br>290                      295                    300 | 912 |
| ttt aag ctt cat ttg tta aag aat atg cct gtg aaa ctt gat aag gta<br>Phe Lys Leu His Leu Leu Lys Asn Met Pro Val Lys Leu Asp Lys Val<br>305                      310                    315                    320 | 960 |
| gaa atg tag cag cct ctc att taa taa tct gat ggg gct tct gtt ttt<br>Glu Met     Gln Pro Leu Ile         Ser Asp Gly Ala Ser Val Phe<br>              325                    330                    335 | 1008 |
| cca cat aga atg ggt tgt ttc tgc taa ggg cta cag agg agg aaa gtc<br>Pro His Arg Met Gly Cys Phe Cys     Gly Leu Gln Arg Arg Lys Val<br>          340                    345                    350 | 1056 |
| act ggc aaa act tcc gtg acc aaa tat cct gaa att agt att ttt tta<br>Thr Gly Lys Thr Ser Val Thr Lys Tyr Pro Glu Ile Ser Ile Phe Leu<br>355                      360                    365 | 1104 |
| aaa aga cct tat ttt gag ttt tca gtt aca taa aaa agc aga agc aga<br>Lys Arg Pro Tyr Phe Glu Phe Ser Val Thr     Lys Ser Arg Ser Arg<br>370                      375                    380 | 1152 |
| ttg gtt tcc taa gtg agc atc gtt tgt gag aat ttt tag tca gtg ttt<br>Leu Val Ser     Val Ser Ile Val Cys Glu Asn Phe     Ser Val Phe<br>385                      390                    395                    400 | 1200 |
| tga aca att att gtt ttt cta agc ttc gtg ttg act ttc tct gat gcg<br>    Thr Ile Ile Val Phe Leu Ser Phe Val Leu Thr Phe Ser Asp Ala<br>                    405                    410                    415 | 1248 |
| tag aaa agt gtt cta acg tag cca agg tta agc cgc tgt cac tac tga<br>    Lys Ser Val Leu Thr     Pro Arg Leu Ser Arg Cys His Tyr<br>                    420                    425                    430 | 1296 |
| aat gct aag aat ttt cct ctt ttc ccg tag tgt aga ggg gta ggg tgt<br>Asn Ala Lys Asn Phe Pro Leu Phe Pro     Cys Arg Gly Val Gly Cys<br>              435                    440                    445 | 1344 |
| ggg aag aag ccg tgt tag cac atc tgt agt att ctg tgt gta tgc tta<br>Gly Lys Lys Pro Cys     His Ile Cys Ser Ile Leu Cys Val Cys Leu<br>450                      455                    460 | 1392 |
| gaa cca gcg tag acc gga tgg gag gat gga cta ggc cta atc cct ccc | 1440 |

```
               Glu Pro Ala     Thr Gly Trp Glu Asp Gly Leu Gly Leu Ile Pro Pro
               465                 470                 475                 480 aac tgg tgg atg tga aga ggt cag gta gga agg cac agg agg gtc acc          1488
Asn Trp Trp Met     Arg Gly Gln Val Gly Arg His Arg Arg Val Thr
                485                 490                 495 act gtc aca gca gtg cca tgc aga cat cct agg aga aga cat ggc agt          1536
Thr Val Thr Ala Val Pro Cys Arg His Pro Arg Arg Arg His Gly Ser
            500                 505                 510 gtt tct tct cag tgc ttc ttc cct taa ctg agc tct gct cac aga cag          1584
Val Ser Ser Gln Cys Phe Phe Pro     Leu Ser Ser Ala His Arg Gln
            515                 520                 525 cta gaa tag att tta act gta aca gaa acc taa atg taa tta aaa cct          1632
Leu Glu     Ile Leu Thr Val Thr Glu Thr     Met     Leu Lys Pro
        530                 535                 540 ggt ctt cct tgg taa gca gac tta aaa tat ctg tat agt aca tgc aag          1680
Gly Leu Pro Trp     Ala Asp Leu Lys Tyr Leu Tyr Ser Thr Cys Lys
545                 550                 555                 560 tgg aaa att tgg gaa tgc gtg tct ctg aat aca tac cgg aag ggc tac          1728
Trp Lys Ile Trp Glu Cys Val Ser Leu Asn Thr Tyr Arg Lys Gly Tyr
                565                 570                 575 tat tac ctt ttc ctt acc att tat act tac cta atg gaa acg agc ttg          1776
Tyr Tyr Leu Phe Leu Thr Ile Tyr Thr Tyr Leu Met Glu Thr Ser Leu
            580                 585                 590 ttt taa cta tca gaa cac tat ttt gta agg tgc tgc aaa gac agt tga          1824
Phe     Leu Ser Glu His Tyr Phe Val Arg Cys Cys Lys Asp Ser
        595                 600                 605 agt ttt cat tac caa ctt ccc caa taa acc agg tgt tca aaa aaa a            1870
Ser Phe His Tyr Gln Leu Pro Gln     Thr Arg Cys Ser Lys Lys
610                 615                 620

<210> SEQ ID NO 2
<211> LENGTH: 223
<212> TYPE: PRT
<213> ORGANISM: Mus sp.

<400> SEQUENCE: 2

Phe Ser Arg Gly Val Ser Ala Arg Arg Thr Thr Leu Gly Arg Cys Ser
 1               5                  10                  15

Cys Pro Ala Phe Leu Arg Ser Ala Pro Ala Ala Thr Asp Asp Met Leu
            20                  25                  30

Arg Cys Gly Leu Ala Cys Glu Arg Cys Arg Trp Ile Leu Pro Leu Leu
        35                  40                  45

Leu Leu Ser Ala Ile Ala Phe Asp Ile Ile Ala Leu Ala Gly Arg Gly
    50                  55                  60

Trp Leu Gln Ser Ser Asn His Ile Gln Thr Ser Ser Leu Trp Trp Arg
65                  70                  75                  80

Cys Phe Asp Glu Gly Gly Gly Ser Gly Ser Tyr Asp Asp Gly Cys Gln
                85                  90                  95

Ser Leu Met Glu Tyr Ala Trp Gly Arg Ala Ala Ala Thr Leu Phe
            100                 105                 110

Cys Gly Phe Ile Ile Leu Cys Ile Cys Phe Ile Leu Ser Phe Phe Ala
        115                 120                 125

Leu Cys Gly Pro Gln Met Leu Val Phe Leu Arg Val Ile Gly Gly Leu
    130                 135                 140

Leu Ala Leu Ala Ala Ile Phe Gln Ile Ile Ser Leu Val Ile Tyr Pro
145                 150                 155                 160

Val Lys Tyr Thr Gln Thr Phe Arg Leu His Asp Asn Pro Ala Val Asn
                165                 170                 175
```

```
Tyr Ile Tyr Asn Trp Ala Tyr Gly Phe Gly Trp Ala Ala Thr Ile Ile
            180                 185                 190

Leu Ile Gly Cys Ser Phe Phe Phe Cys Cys Leu Pro Asn Tyr Glu Asp
        195                 200                 205

Asp Leu Leu Gly Ala Ala Lys Pro Arg Tyr Phe Tyr Pro Pro Ala
    210                 215                 220

<210> SEQ ID NO 3
<211> LENGTH: 33
<212> TYPE: PRT
<213> ORGANISM: Mus sp.

<400> SEQUENCE: 3

Cys Gly Arg Lys Ser Leu Arg Lys Ala Cys Cys Lys Met Asp Leu Arg
  1               5                  10                  15

Arg Lys Leu Phe Ser Lys Ala Gln Gly Thr Tyr Val Trp Ala Met Phe
                20                  25                  30

Ile

<210> SEQ ID NO 4
<211> LENGTH: 5
<212> TYPE: PRT
<213> ORGANISM: Mus sp.

<400> SEQUENCE: 4

Ser Glu Met Leu Glu
  1               5

<210> SEQ ID NO 5
<211> LENGTH: 8
<212> TYPE: PRT
<213> ORGANISM: Mus sp.

<400> SEQUENCE: 5

Met Leu Lys Lys Ile Leu His Asn
  1               5

<210> SEQ ID NO 6
<211> LENGTH: 11
<212> TYPE: PRT
<213> ORGANISM: Mus sp.

<400> SEQUENCE: 6

Val Ser Cys Met Ser Cys Gly Val Lys Lys Thr
  1               5                  10

<210> SEQ ID NO 7
<211> LENGTH: 35
<212> TYPE: PRT
<213> ORGANISM: Mus sp.

<400> SEQUENCE: 7

Ile Leu Phe Ala Lys Tyr Met Leu Ile Phe Pro Tyr Val Asn Ser Ile
  1               5                  10                  15

Pro Phe Lys Leu His Leu Leu Lys Asn Met Pro Val Lys Leu Asp Lys
                20                  25                  30

Val Glu Met
        35

<210> SEQ ID NO 8
<211> LENGTH: 4
```

```
<212> TYPE: PRT
<213> ORGANISM: Mus sp.

<400> SEQUENCE: 8

Gln Pro Leu Ile
  1

<210> SEQ ID NO 9
<211> LENGTH: 15
<212> TYPE: PRT
<213> ORGANISM: Mus sp.

<400> SEQUENCE: 9

Ser Asp Gly Ala Ser Val Phe Pro His Arg Met Gly Cys Phe Cys
  1               5                  10                  15

<210> SEQ ID NO 10
<211> LENGTH: 33
<212> TYPE: PRT
<213> ORGANISM: Mus sp.

<400> SEQUENCE: 10

Gly Leu Gln Arg Arg Lys Val Thr Gly Lys Thr Ser Val Thr Lys Tyr
  1               5                  10                  15

Pro Glu Ile Ser Ile Phe Leu Lys Arg Pro Tyr Phe Glu Phe Ser Val
             20                  25                  30

Thr

<210> SEQ ID NO 11
<211> LENGTH: 8
<212> TYPE: PRT
<213> ORGANISM: Mus sp.

<400> SEQUENCE: 11

Lys Ser Arg Ser Arg Leu Val Ser
  1               5

<210> SEQ ID NO 12
<211> LENGTH: 8
<212> TYPE: PRT
<213> ORGANISM: Mus sp.

<400> SEQUENCE: 12

Val Ser Ile Val Cys Glu Asn Phe
  1               5

<210> SEQ ID NO 13
<211> LENGTH: 15
<212> TYPE: PRT
<213> ORGANISM: Mus sp.

<400> SEQUENCE: 13

Thr Ile Ile Val Phe Leu Ser Phe Val Leu Thr Phe Ser Asp Ala
  1               5                  10                  15

<210> SEQ ID NO 14
<211> LENGTH: 5
<212> TYPE: PRT
<213> ORGANISM: Mus sp.

<400> SEQUENCE: 14

Lys Ser Val Leu Thr
  1               5
```

```
<210> SEQ ID NO 15
<211> LENGTH: 8
<212> TYPE: PRT
<213> ORGANISM: Mus sp.

<400> SEQUENCE: 15

Pro Arg Leu Ser Arg Cys His Tyr
  1               5

<210> SEQ ID NO 16
<211> LENGTH: 9
<212> TYPE: PRT
<213> ORGANISM: Mus sp.

<400> SEQUENCE: 16

Asn Ala Lys Asn Phe Pro Leu Phe Pro
  1               5

<210> SEQ ID NO 17
<211> LENGTH: 11
<212> TYPE: PRT
<213> ORGANISM: Mus sp.

<400> SEQUENCE: 17

Cys Arg Gly Val Gly Cys Gly Lys Lys Pro Cys
  1               5                  10

<210> SEQ ID NO 18
<211> LENGTH: 13
<212> TYPE: PRT
<213> ORGANISM: Mus sp.

<400> SEQUENCE: 18

His Ile Cys Ser Ile Leu Cys Val Cys Leu Glu Pro Ala
  1               5                  10

<210> SEQ ID NO 19
<211> LENGTH: 16
<212> TYPE: PRT
<213> ORGANISM: Mus sp.

<400> SEQUENCE: 19

Thr Gly Trp Glu Asp Gly Leu Gly Leu Ile Pro Pro Asn Trp Trp Met
  1               5                  10                  15

<210> SEQ ID NO 20
<211> LENGTH: 35
<212> TYPE: PRT
<213> ORGANISM: Mus sp.

<400> SEQUENCE: 20

Arg Gly Gln Val Gly Arg His Arg Val Thr Thr Val Thr Ala Val
  1               5                  10                  15

Pro Cys Arg His Pro Arg Arg Arg His Gly Ser Val Ser Ser Gln Cys
                 20                  25                  30

Phe Phe Pro
         35

<210> SEQ ID NO 21
<211> LENGTH: 9
<212> TYPE: PRT
<213> ORGANISM: Mus sp.

<400> SEQUENCE: 21
```

Leu Ser Ser Ala His Arg Gln Leu Glu
 1               5

<210> SEQ ID NO 22
<211> LENGTH: 7
<212> TYPE: PRT
<213> ORGANISM: Mus sp.

<400> SEQUENCE: 22

Ile Leu Thr Val Thr Glu Thr
 1               5

<210> SEQ ID NO 23
<211> LENGTH: 7
<212> TYPE: PRT
<213> ORGANISM: Mus sp.

<400> SEQUENCE: 23

Leu Lys Pro Gly Leu Pro Trp
 1               5

<210> SEQ ID NO 24
<211> LENGTH: 44
<212> TYPE: PRT
<213> ORGANISM: Mus sp.

<400> SEQUENCE: 24

Ala Asp Leu Lys Tyr Leu Tyr Ser Thr Cys Lys Trp Lys Ile Trp Glu
 1               5                  10                  15

Cys Val Ser Leu Asn Thr Tyr Arg Lys Gly Tyr Tyr Tyr Leu Phe Leu
                20                  25                  30

Thr Ile Tyr Thr Tyr Leu Met Glu Thr Ser Leu Phe
            35                  40

<210> SEQ ID NO 25
<211> LENGTH: 13
<212> TYPE: PRT
<213> ORGANISM: Mus sp.

<400> SEQUENCE: 25

Leu Ser Glu His Tyr Phe Val Arg Cys Cys Lys Asp Ser
 1               5                  10

<210> SEQ ID NO 26
<211> LENGTH: 8
<212> TYPE: PRT
<213> ORGANISM: Mus sp.

<400> SEQUENCE: 26

Ser Phe His Tyr Gln Leu Pro Gln
 1               5

<210> SEQ ID NO 27
<211> LENGTH: 6
<212> TYPE: PRT
<213> ORGANISM: Mus sp.

<400> SEQUENCE: 27

Thr Arg Cys Ser Lys Lys
 1               5

DNA SEQUENCE ENCODING THE P99 GENE AND KITS FOR THE DETECTION OF NEOPLASIA

REFERENCE TO RELATED APPLICATIONS

This patent application is a continuation of United States Provisional Patent Application, entitled Metastatic Sequences, Ser. No. 60/077,934, filed Mar. 13, 1998.

RIGHTS IN THE INVENTION

The invention was made with support from the United States government under grant numbers RO1-CA50588, RO1-CA68814 and P50-CA58204, awarded by the National Institutes of Health, and the United States government has certain rights in this invention.

BACKGROUND OF THE INVENTION

1. Field of the Invention

The present invention relates to methods for the identification, isolation and use of metastatic genes and their sequences, to sequences identified by these methods, and to the use of diagnostic and therapeutic agents based on these sequences for the treatment of metastatic and other neoplastic disorders.

2. Description of the Background

The development of higher organisms is characterized by an exquisite pattern of temporal and spatially regulated cell division. Disruptions in the normal physiology of cell division are almost invariably detrimental. One such type of disruption is cancer, a disease that can arise from a series of genetic events.

Cancer cells are defined by two heritable properties, uncontrolled growth and uncontrolled invasion of normal tissue. A cancerous cell can divide in defiance of the normal growth constraints in a cell leading to a localized growth or tumor. In addition, some cancer cells also gain the ability to migrate away from their initial site and invade other healthy tissues in a patient. It is the combination of these two features that make a cancer cell especially dangerous.

An isolated abnormal cell population that grows uncontrollably will give rise to a tumor or neoplasm. As long as the neoplasm remains noninvasively in a single location, it is said to be benign, and a complete cure may be expected by removing the mass surgically. A tumor or neoplasm is counted as a cancer if it is malignant, that is, if its cells have the ability to invade surrounding tissue. True malignancy begins when the cells cross the basal lamina and begin to invade the underlying connective tissue. Malignancy also occurs when the cells gain the ability to detach from the main tumor mass, enter the bloodstream or lymphatic vessels, and form secondary tumors or metastases at other sites in the body. The more widely a tumor metastasizes, the harder it is to eradicate and treat.

As determined from epidemiological and clinical studies, most cancers develop in slow stages from mildly benign into malignant neoplasms. Malignant cancer usually begins as a benign localized cell population with abnormal growth characteristics called dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the more clear examples of the progression of normal tissue to benign neoplasm to malignant neoplasm.

Prostate cancer is the most common malignancy in men in the USA, resulting in an estimated 41,800 deaths in 1997. (Parker S L, et al., *CA Cancer J Clin* 47: 5–27, 1997). The widespread use of prostate-specific antigen (PSA) has dramatically increased the number of patients diagnosed with prostate cancer and generally lowered the stage of disease at diagnosis. (Scardino P T, *Urol. Clin. N. Am.* 16:635–655, 1989; Epstein J L, et al., *JAMA* 271: 368–374, 1994). Nevertheless, 5%–10% of cancers detected by PSA screening are clinically advanced and not candidates for radical prostatectomy. Despite surgical removal of the prostate, 30%–60% of men treated will have recurrence of cancer within 5 years, suggesting that the clinical stage of the patients undergoing surgery was highly inaccurate. 20%–57% of patients undergoing definitive surgery with presumed localized disease will have rising PSA following treatment, also indicative of local or distant residual disease. (Ohori M, et al., *J. Urol.* 154: 1818–1824, 1995; Zeitman AL, et al., *Urology* 43: 828–833, 1994). Neither of these conditions is amenable to curative therapy.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma, a type of neoplasia. BPH is very common in men over the age of 50. It is characterized by the presence of a number of large distinct nodules in the periurethral area of the prostate. Although benign and not malignant, these nodules can produce obstruction of the urethra causing nocturia, hesitancy to void, and difficulty in starting and stopping a urine stream upon voiding the bladder. Left untreated, a percentage of these prostate hyperplasias and neoplasias may develop into malignant prostatic carcinoma.

In its more aggressive form, malignant transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with prostatic carcinoma. Local invasion typically involves the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that about 60% of newly diagnosed prostate cancer patients will have metastases at the time of initial diagnosis.

Surgery or radiotherapy is the treatment of choice for early prostatic neoplasia. Surgery involves complete removal of the entire prostate (radical prostatectomy), and often removal of the surrounding lymph nodes, or lymphadenectomy. Radiotherapy, occasionally used as adjuvant therapy, may be either external or interstitial using $^{125}$I. Endocrine therapy is the treatment of choice for more advanced forms. The aim of this therapy is to deprive the prostate cells, and presumably the transformed prostate cells as well, of testosterone. This is accomplished by orchiectomy (castration) or administration of estrogens or synthetic hormones which are agonists of luteinizing hormone-releasing hormone. These cellular messengers directly inhibit testicular and organ synthesis and suppress luteinizing hormone secretion which in turn leads to reduced testosterone secretion by the testes. In normal prostate, removal of androgenic hormones results in regression of the gland involving apoptosis of more than 60% of the luminal epithelial cells. Although often initially sensitive to removal of androgens, prostate cancer cells eventually lose this response and continue to grow and spread even in the absence of androgenic steroids. Despite the advances made in achieving a pharmacologic orchiectomy, the survival rates for those with late stage carcinomas are rather bleak.

Current therapeutic regimens for metastatic disease typically involve both chemical and surgical androgen ablation, which although has been demonstrated to extend life when compared to untreated patients, almost invariably results in the development of hormone-refractory disease and the demise of the patient. The fundamental concepts upon which current androgen ablation therapy was developed were reported more than 50 years ago by Huggins and Hodges. (Huggins C, et al., *Cancer Res.* 1:293–297, 1941). These experiments reported the phenomenon in which removal of androgenic steroids by castration resulted in reduced growth and biochemical activities in prostate cancer.

With the advent of molecular biology, various investigators in laboratories have attempted to understand the molecular biology of castration-induced regression of the prostate at a more mechanistic level. The model systems selected almost invariably compared mRNAs produced prior to castration and during castration-induced regression using rat prostate model systems in vivo. These model systems yield gene activities that may be involved in castration-induced regression but could also be involved in activities that are not directly relevant or related to castration-induced regression but were stimulated by removal of androgenic steroids. It is anticipated that only a small fraction of gene activities modulated by steroid withdrawal would indeed be involved in castration-induced regression and, therefore, significant confounding background activity would be seen in these existing model systems. There is therefore a need for a model system in which the androgenic-stimulated gene activities not associated with castration-induced regression, or "background" gene activities, would be normalized. Moreover, a better understanding of the molecular basis of metastasis, in prostate cancer, as well as other forms of cancer, would allow rational efforts toward the development of novel effective anti-metastatic therapy to proceed.

SUMMARY OF THE INVENTION

The present invention overcomes the problems and disadvantages associated with current strategies and designs and provides new compositions and methods for the for the evaluation, diagnosis and treatment of metastatic and other neoplastic disorders.

One embodiment of the invention is directed to compositions and methods for treating a patient having a metastatic tumor. Compositions may contain agents that selectively target metastatic cells for destruction. Such agents include nucleic acid sequences that selectively suppress metastasis or protein sequences that selectively destroy metastatic cells. Methods involve administering a therapeutically effective amount of, for example, an anti-sense nucleic acid that selectively suppresses expression of a gene encoding a metastatic-specific protein or metastatic-specific protein that selectively inhibits the proliferation of or destroys the metastatic cell, to the patient. The nucleic acid may comprise, for example, RNA, DNA or PNA, and be expressed using any suitable means, such as a viral vector which is a vector containing one or more virally-derived sequences. Useful viral vectors include vaccinia virus vectors, herpes virus vectors, retrovirus vectors, adenovirus vectors, adeno-associated virus vectors, lenti viral vectors and combinations thereof. The anti-sense sequence may encode the entirety of or, alternately, an effective portion of the gene encoding the metastatic sequence, such as a functional domain like a scaffolding domain or a dimerization domain. Alternately, the effective portion may comprise the transcription promoter region of the gene.

Another embodiment of the invention is directed to methods for treating a metastatic disorder, such as metastatic prostate or breast cancer, by administering to a patient having the disorder an effective amount of an anti-sense sequence, a metastatic-specific product or an antibody to such products. The antibody may be reactive against all or an effective portion of the sequence or its product, such as the scaffolding domain or the dimerization domain of a caveolin protein.

Another embodiment of the invention is directed to methods for evaluating the metastatic potential of a primary prostate tumor by contacting a sample of the tumor with an antibody to the product of the metastatic sequence coupled to a detectable marker and then determining the amount of antibody bound to the sample. The antibody may be a monoclonal or polyclonal antibody, and may be optionally coupled to a detectable label.

Another embodiment of the invention is directed to methods for treating a metastatic disorder, such as a metastatic prostate cancer, by administering to a patient having the disorder an effective amount of the metastatic sequence, said metastatic sequence functioning as a metastatic suppressor, such as lysyl oxidase. Transcription of the metastatic sequence may be driven by a promoter that is up-regulated by metastasis-specific factors in metastatic cells, such as the caveolin promoter.

Another embodiment of the invention is directed to methods for treating a neoplastic disorder, preferably a metastatic disorder, comprising administering a pharmaceutically effective amount of a metastatic nucleic acid to a patient. The nucleic acid may be single stranded in the sense or the anti-sense direction. Alternatively, the nucleic acid may be packaged in a viral vector such as, for example, herpes viral vectors, retroviral vectors, adenoviral vectors, adeno-associated viral vectors, lenti viral vectors, vaccinia viral vectors and combinations thereof. Administration may be performed by injection, pulmonary absorption, topical application or delayed release of the nucleic acid along with a pharmaceutically acceptable carrier such as water, alcohols, salts, oils, fatty acids, saccharides, polysaccharides and combinations thereof.

Another embodiment of the invention is directed to isolated promoters that are specific for expression in metastatic cells. The promoter may further be functionally coupled to a gene which encodes an anti-metastatic therapeutic agent. The therapeutic agent may be a toxin, an apoptotic inducer, a cytokine such as IL-2 or IL-12, or another suitable agent or combination of agents.

Another embodiment of the invention is directed to methods for the isolation of a metastatic sequence. One or more oncogenic sequences are transfected into a cell to form a transfected cell. The transfected cell is introduced into a primary site of a host animal to establish a colony which is incubated in the animal for a period of time sufficient to develop both a primary tumor an d a malignant tumor. RNA is harvested from the primary tumor and from the malignant tumor and the two groups of RNA sequences are compared to each other. The harvested tumor RNAs are also compared to normal nonmalignant tissues to identify sequences specific for nonmetastatic tumors as well as those specific for metastatic tumors. Dominant metastatic genes are genes whose expression leads to metastasis. Such genes are typically expressed at high levels in metastatic tumors and not significantly expressed in normal or nonmetastatic cells. Recessive metastatic genes, genes whose expression prevents metastasis, may be selectively expressed in normal and nonmetastatic cells and absent in metastatic cells. Dominant and recessive metastatic genes may act directly or act pleiotropically by enhancing or inhibiting the expression or function of other dominant and recessive metastatic genes.

Another embodiment of the invention is directed to sequences isolated by the methods of the invention. Sequences may be in the form of DNA, RNA or PNA. The nucleic acid may be single stranded or double stranded. Single stranded nucleic acid may be in the form of a sense strand or an anti-sense strand. In addition, the sequence may be part of a homologous recombination vector designed to recombine with another metastatic sequence.

Another embodiment of the invention is directed to methods for the identification of metastatic sequences. One or more oncogenic sequences are transfected into a mammalian urogenital cell to form a transfected cell. The transfected cell is introduced into a site of a host animal and incubated for a period of time sufficient for cells to proliferate and to develop malignancies at secondary sites. RNA is isolated from the primary and secondary sites and reverse transcribed into cDNA. cDNA sequences from the primary tumor and the secondary metastasis are compared by differential display polymerase chain reaction to detect and subsequently isolate metastatic sequences. The host mammal may be an allogenic, a xenogenic, a transgenic or an immunocompromised host.

Another embodiment of the invention is directed to kits that contain one or more metastatic sequences that can be used for staging a tumor. DNA or RNA may be isolated from a tumor and detected using a probe comprising a metastatic sequence. The presence or absence of metastatic DNA or RNA sequences in the tumor, will indicate the oncogenic and metastatic potential of the tumor.

Other objects and advantages of the invention are set forth in part in the description which follows, and in part, will be obvious from this description, or may be learned from the practice of the invention.

DESCRIPTION OF THE DRAWINGS

FIG. 1 Nucleotide and amino acid sequences of p99 (SEQ ID NO:1).

FIG. 2 A compilation of the sequences obtained using methods of the invention for identifying dominant and recessive metastatic sequences.

FIG. 3 Data obtained through the initial characterization of some of the sequences resulting from the Met screen.

FIG. 4 Data obtained through the initial characterization of some of the sequences (also) resulting from the Met screen.

FIG. 5 Data obtained through the initial characterization of some of the sequences (also) resulting from the Met screen.

FIG. 6 Data obtained through the initial characterization of some of the sequences (also) resulting from the p53 screen.

FIG. 7 Data obtained through the initial characterization of some of the sequences (also) resulting from the TGF-β screen.

FIG. 8 Data obtained through the initial characterization of some of the sequences resulting from screening a phage library.

FIG. 9 Summaries of study results on the expression of the metastatic sequences in primary cells and in metastatic cells using RNA blots.

DESCRIPTION OF THE INVENTION

Identification of Metastatic Sequences

As embodied and broadly described herein, the present invention is directed to compositions and methods for detection, diagnosis, treatment and prevention of metastatic disease and disorders.

The ability of cancers to metastasize makes tumors difficult to eradicate by any means. Malignant cancer involves a multistage progression from, for example, normal tissue through hyperplasia, early adenoma, early carcinoma and finally to a metastatic tumor. Cells of a typical tumor loosen their adhesion to their original cellular neighbors and cross the basal lamina and endothelial lining to enter the body's circulation. Once in circulation, the metastatic cell exits from the circulation to disseminate throughout the body and proliferate in a new environment.

Like the initial oncogenic event, the ability of a cell to metastasize requires additional mutations or epigenetic changes. An understanding of the molecular mechanisms of metastasis allows for the design of treatments to inhibit metastasis. Knowledge of stage specific gene expression for neoplastic disorders allows for early detection and typing of tumors. With early detection and typing, proper treatment may be administered to a patient with the neoplastic disorder earlier, which will lead to a higher probability of a complete cure.

For human prostate tumors, the study of stage specific tumors is difficult, if not impossible, as cell lines are extremely difficult to grow and it is rare that tissue becomes available from the primary tumor as well as metastatic disease from the same patient. This problem is exacerbated because of the infrequent biopsy of metastatic deposits in concordance of isolation of material from the primary tumor. Furthermore, the growth of cell lines from malignant prostates has proved to be problematic over the last few decades. This is evidenced by the lack of cell lines from prostate cancer obtained under any conditions.

Expression metastatic sequences are either increased or decreased in metastatic cancer cells as compared to primary tumors depending upon the function of the sequence. Recessive metastatic genes functioning as tumor suppressors are down-regulated in metastatic cells while dominant metastatic genes are up-regulated. Using the methods of the present invention, certain cancers may be treated, for example, by either suppressing or inducing the expression, as the situation requires, of these genes in metastatic cells or cells predisposed to metastasis. As expression correlates with metastasis, application of biological technologies designed to either block activity or up-regulate the activity of these genes or their products and may be used for the treatment and prevention of metastatic and other neoplastic disorders. Variations of conventional techniques that take advantage of this observation can also be used for the treatment and prevention of metastatic disease.

One embodiment of the invention is directed to a method for identifying a metastatic sequence. A mammalian cell is transformed into a pre-neoplastic or neoplastic state or phenotype by transfection with one or more oncogenic sequences (e.g. DNA, RNA, PNA). Alternatively, or in addition to transfection, the mammalian cell may be treated with an agent or subjected to a condition that potentiates the metastatic character of the cell or predisposes the cell to metastasis. The transfected or treated cell is implanted into a host animal at a primary site and grown for a period of time sufficient to develop a metastasis at a secondary site. Expressed sequences from cells of the primary site and cells at the secondary site are amplified by differential display polymerase chain reactions. PCR products from these reactions are compared and the metastatic sequence identified by alteration in the levels or patterns of the resulting products.

Mammalian cells from a wide variety of tissue types and species are suitable for transfection or treatment including surgically obtained or primary or immortalized cells and cell lines. Cells may be from humans or primates, mice, rats, sheep, cows, rabbits, horses, pigs or guinea pigs or from transgenic or xenogeneic host mammals. Cells may be obtained from adult, juvenile or fetal tissue, and used directly from the mammal, from cryogenically preserved samples, or after culturing in vitro or in vivo for a period of time. In vitro culturing typically involves tissue culture conditions (e.g. 37° C., 5% $CO_2$) while in vivo culturing may involve successive passage of cells through host animals such as, for example, mice or rabbits. Cells passed in vivo may be obtained from sites proximal or distal to the site of implantation. The tissue type from which the cells are derived or obtained may be any tissue which is susceptible to transfection, or other treatment including, for example, urogenital tissues, epithelial cells, hepatic cells, fibroblasts lymphatic tissues, hematopoietic cells, cells of the immune system, cells of the gastrointestinal system and cells of the nervous system.

Starting cells may also be treated prior to use to enhance detection sensitivity. Treatment may comprise contact with reagents which affects the neoplastic, metastatic, differentiation, activation or growth of the cell. Treatment may be in vitro or in vivo and may include, for example, direct or indirect induction or suppression of well known oncogenic sequences and genes isolated by the invention such as, for example, TGF-β1, cyclin D1, p53, lysyl oxidase, caveolin, actin binding protein, ubiquitin activating enzyme E1, nmb, α actinin 3, and p34. Gene expression induction includes transfecting expression vectors encompassing the coding region of the gene. Gene repression comprises introducing a gene ablation sequence or a repressor of the gene to the cell.

Cells which have one or more genes ablated may also be used. For example a metastatic suppression gene may be ablated to prevent inhibition to metastasis. A useful gene for ablation is a gene capable of affecting the phenotype and behavior of a cell or tumor. For example, with prostate tumors, suitable genes include both well known genes and genes isolated by the methods of the invention such as for example, TGF-β1, cyclin D1, p21, p34, p53, lysyl oxidase, caveolin, actin binding protein, ubiquitin activating enzyme E1, nmb, and α actinin 3. Genetic ablation (gene knockout) refers to a process of silencing the expression of a particular gene in a cell. The silencing process may include for example, gene targeting or anti-sense blocking. Gene targeting refers to a process of introducing a nucleic acid construct into a cell to specifically recombine with a target gene. The nucleic acid construct inactivates the targeted gene. Inactivation may be by introduction of termination codons into a coding region or introduction of a repression site into a regulatory sequence. Anti-sense blocking refers to the incorporation into a cell of expression sequences which directs the synthesis of anti-sense RNA to block expression of a target gene. Anti-sense RNA hybridizes to the mRNA of the target gene to inhibit expression.

Another embodiment of the invention is directed to analysis of a cell line before it is used as starting material to isolate metastatic genes in a particular pathway. Analysis is useful in identifying cells, and consequently sequences specific to these cells, which are particularly susceptible or resistant to metastatic transformation. For example, a cell highly predisposed to metastasis may be especially sensitive for detecting metastatic genes. Conversely, a cell showing high resistance to metastasis can be used to isolate especially potent metastatic sequences. One method to analyze susceptibility to metastasis is to determine the cellular response to growth factors or growth inhibitors. Briefly, a control population and a test population of cells are exposed to a growth factor or a growth inhibitor and the cellular response (e.g. proliferation, metabolism) recorded. Cells showing abnormal responses to the growth factor or growth inhibitor may be used as the starting material for metastatic gene isolation. Cellular responses include changes in the rate of cellular division (e.g. thymidine uptake), changes in the expression of RNA and/or proteins, changes in cellular localization or modification of patterns of RNA and/or proteins, and changes in the rate of uptake, release or metabolism of nutrients.

Especially potent or weak metastatic genes may be detected by treating and analyzing the metastatic potential of different cells and selecting a suitable cell type as the starting material. For example, cells may be treated with myc, ras and p53 or combinations thereof, and analyzed for cyclin D1 expression which is shown to correlate with metastasis. The gene expression pattern of cyclin D1 in MPR correlates with that of human prostate tumors analyzed with stains specific for cyclin D1 expression. Normal human tissue shows no cyclin D1 expression or staining. Moderately differentiated prostate cancers with dispersed or focal positive staining show moderate staining. Advanced, poorly differentiated prostate cancer shows strong nuclear as well as cytoplasmic staining implying strong expression of cyclin D1. After treatment with myc, ras or p53, cyclin D1 expression shows correlation with the metastatic potential of the cell. Thus, cyclin D1 expressing cells are a source of cells with high metastatic potential. Conversely, cells with low cyclin D1 expression are a source of potentially metastatically resistant cells.

This method may be adjusted for the isolation of metastatic sequences expressed along a particular developmental or differentiation pathway by combining the various treatment and analytical techniques. For example, a mammalian cell may be genetically ablated for TGF-β1, Cyclin D1; p53, lysyl oxidase., caveolin, actin binding protein, ubiquitin activating enzyme E1, nmb, α actinin 3, or p34. The genetically altered cell is used in an in vivo mouse prostate reconstitution (MPR) model. Metastatic and nonmetastatic cells isolated from the MPR may be analyzed directly or after induction with an agent such as the TGF-β gene or its product. Analysis involves the use of differential display polymerase chain reaction to identify differentially expressed bands. Sequences identified may be used for subsequent gene ablation, transformation or differential analysis.

Cell types useful for the identification of metastatic sequences related to prostate cancer include cells and cell lines of the fetal prostate lineage from normal or transgenic animals. Prostate cells may be derived from normal prostates or from reconstituted prostate tissue. One method of generating reconstituted prostate cells is to isolate fetal prostate tissue and micro dissect the fetal prostate epithelium away from fetal mesenchyme. Fetal prostate epithelium may be genetically manipulated before reassociation with fetal mesenchyme. Genetic manipulation involves treatment or transfection with a metastatic agent or nucleic acid sequence that affects neoplastic or metastatic potential of the cell. Reassociation of fetal epithelium and mesenchyme is performed by implanting epithelial tissue within a pocket of mesenchymal tissue. After manipulation, cells are reimplanted into a mammalian host in a similar manner as other cells, such as reimplantation into or under the renal capsule.

The metastatic potential of a cell may be altered, for example, by gene ablation with a sequence specific for a recessive oncogene. Recessive oncogenes are those genes which encode products which can suppress oncogenesis and metastasis. A gene ablation sequence can be designed to specifically suppress a recessive oncogene. Ablation may include pre-transcriptional inhibition such as homologous recombination with endogenous recessive oncogenes and post transcriptional inhibition such as the expression of anti-sense oncogenes to suppress translation. Gene ablation sequences may be targeted towards well known recessive oncogenes such as, for example, the retinoblastoma gene (Rb) or Bcl. Other candidates for ablation include metastatic genes previously isolated by the invention such as, for example, TGF-β1, cyclin D1 , p21, p34, p53, lysyl oxidase, caveolin, actin binding protein, ubiquitin activating enzyme E1, nmb and α-actinin-3. The effects of ablating a recessive oncogene may include oncogenesis and metastases.

Genetic ablation (gene knockout) may be performed after a cell is selected for use or a cell already comprising a genotype with the proper genetic ablation may be selected. Cells already comprising gene ablation may be acquired from a cell depository, from other laboratories or from a transgenic animal. A transgenic animal which comprises a genetically ablated gene will carry the genotype in every cell in its body. Thus, any tissue from a transgenic animal may be used as the starting material.

After selection, the cell is transformed with an oncogenic sequence. An oncogene is a sequence which can predispose, or induce the cell into a pre-neoplastic or neoplastic condition or otherwise enhance the metastatic potential of the cell. Oncogenes can be classified into two types, dominant oncogenes and recessive oncogenes. One or more dominant oncogenes can confer a neoplastic or preneoplastic phenotype to a cell when transfected. One or more recessive oncogenes, when silenced, may also confer a neoplastic or preneoplastic phenotype. Gene silencing is performed by transfecting cells with nucleic acids which cause genetic ablation or by anti-sense suppression. While any oncogene may be used, the preferred oncogenes are those that are normally associated with prostate tumors. Thus, TGF-β1, Cyclin D1 , p53, lysyl oxidase, caveolin, actin binding protein, ubiquitin activating enzyme E1, nmb, α actinin 3, or p34 are among the preferred genes. Other oncogenes which may also be used include abl, ahi, akt, bcl, crk, dsi, erb, ets, evi, fes/fps, fim, fis, fgr, flv, fms, fos, gin, gli, int, jun, kit, mas, lck, met, mil/raf mis, mlv, mos, myb, myc, neu, onc, pim, raf ras, rel, ros, seq, sis, ski, spi, src, tcl, thy, trk, and yes. Metastatic-specific genes may be used individually or in combination with other oncogenes.

Many oncogenes represent members of multigene families or homolog families. Members of a multigene family or a homolog of an oncogene may also be used. Two genes are homologs when they encode for proteins which have very similar primary, secondary or tertiary structures. Thus two genes may differ in nucleic acid sequence or encoded peptide sequence and still be homologs to each other because the confirmation of the encoded polypeptides have similar spatial folding. Homologs genes may have arisen from divergent evolution from a common ancestor or from convergent evolution from different ancestral genes. Convergent evolution refer to the effect of two genes evolving under similar evolutionary pressure to encode proteins which are similar to each other.

Some oncogenes, such as ras, are oncogenic when mutated. Other oncogenes, such as myc, are oncogenic when overexpressed. In using oncogenes for transfection, mutated or overexpress forms of the oncogenes may also be used. Another method to predispose a cell to metastasis and neoplasia is to ablate recessive oncogenes. Ablation may include pre-transcriptional inhibition such as homologous recombination with endogenous recessive oncogenes and post transcriptional inhibition such as the expression of anti-sense oncogenes to suppress translation.

The effects of oncogenes are at least additive and often synergistic. Thus, dominant oncogenes may be transfected together or multiple recessive oncogenes ablated together for a stronger effect. Furthermore, both methods may be combined and dominant oncogene transfection may be accompanied by recessive oncogene ablation.

Genetic manipulation of the starting material may be accomplished by well-established laboratory procedures. Numerous methods, either direct or indirect, have been developed for cellular transfection. Mammalian cells may be transfected by a variety of techniques, ail of which are well-known to those of ordinary skill. Direct methods involve the introduction of genetic material into the nucleus of a cell by injection. These techniques include high velocity projectile injection, microinjection, and electroporation. Indirect methods involve the active or passive uptake of the genetic information by the cell. Indirect techniques include transduction with recombinant vectors, and chemical or physical treatments such as calcium phosphate uptake, lipofection or dextran sulfate transfection. Chemical techniques rely on chemical carriers to introduce nucleic acids into a cell. These methods, for example, utilize unilamellar phospholipid vesicles (e.g. liposomes) loaded with DNA (or RNA). The approach relies on the fusion of the DNA containing vesicles with the plasma membrane of the recipient cells. After entry, DNA traverses the cytoplasm and enters the nucleus. Another lipofection technique uses a synthetic cationic lipid such as N-[1-(2,3-dioieyloxy) propyl]-N,N,N-trimethylammonium chloride (DOTMA). DOTMA spontaneously associates with nucleic acids and forms unilamellar vesicles upon sonication. Genetic material is incorporated into these vesicles and subsequently transfected into the cell. Calcium phosphate co-precipitation involves mixing of,purified nucleic acid with buffers containing phosphate and calcium chloride which results in the formation of a fine precipitate. Presentation of this precipitate to cells results in incorporation of the nucleic acid into cellular genome. Other chemicals, such as DEAE dextran or polybrene, when present in media with nucleic acids, can also cause the transfection of mammalian cells.

Physical methods of transfection rely on electric fields, needles and particles to enable nucleic acids to traverse the cellular membrane. Electric field mediated DNA transfection, commonly called electroporation, is based on the principle that membranes, when subjected to an electric field, undergo a reversible breakdown resulting in pores large enough to permit the passage of nucleic acids. In micro-projectile mediated gene transfer, micro-projectiles of subcellular dimensions are coated with nucleic acid and propelled at high velocity into a cell using a particle gun. The nucleic acid is introduced into the nucleus directly when the particles impinge upon the nucleus. In microinjection, nucleic acid is injected directly into the nucleus of a cell with a needle. Lasers have also been used to introduce minute holes in cellular membranes to allow introduction of nucleic acids. All these methods may be used for transfection and the selection of the method will depend on the cell type, the desired transfection efficiency and the equipment available.

The efficiency of transfection, the fraction of live cells transfected with the oncogene, may be monitored and enhanced by the co-transfection of a selectable marker. If a marker is co-transfected with a genetic construct, positively transformed cells may be separated from nontransformed cells by chemical selection. The efficiency of transfection will be increased in most cases because the chemicals will selectively kill non-transfected cells. The number of transfected cells may also be monitored by analyzing the degree of chemical resistance of the transfected cells. Markers commonly used for selection purposes include, for example, nucleic acids encoding dihydrofolate reductase, metallothionein, CAD, adenosine deaminase, adenylate deaminase, UMP synthetase, IMP 5'-dehydrogenase, xanthine-guanine phosphoribosyltransferase, mutant thymidine kinase, mutant HGPRTase, thymidylate synthetase, P-glycoprotein 170, ribonucleotide reductase, glutamine synthetase, asparagine synthetase, arginosuccinate synthetase, ornithine synthetase, sodium or potassium dependent ATPase or derivatives or mutants of these nucleic acids. Markers may be used individually or in combination. Chemicals useful for selection include methotrexate, cadmium, PALA, Xyl-A, adenosine, 2'-deoxycoformycin, adenine, azaserine, coformycin, 6-azauridine, pyrazofuran, mycophenolic acid, limiting xanthine, hypoxanthine, aminopterin, thymidine, 5-fluorodeoxyuridine, adriamycin, vincristine, colchicine, actinomycin D, puromycin, cytocholasin B, emetine, maytansine, Bakers' antifolate, aphidicolin, methionine sulfoximine, β-aspartyl hydroxamate, albizziin, canavanine, α-difluoromethylornithine, compactin, tunicamycin, borrelidin, ouabain, and derivatives and analogs and combinations of these chemicals. Some chemicals, such as methotrexate, may be used individually while other chemicals, such as HAT (hypoxanthine, aminopterin and thymidine), need to be used in combination to be effective.

Alternatively, or in addition to transfecting the mammalian cell may be treated with an agent, either before or after transfection, that alters the expression of the cell's nucleic acids. Treatment may comprise contacting the cells with one or more agents which affect the neoplastic character (e.g. neoplastic agents; phorbol esters), metabolization (e.g. metabolic agents), metastatic character (e.g. metastatic agents), differentiation (e.g. differentiation agents; retinoic acid), activation or proliferation (e.g. growth factors) of the cell. Agents which can alter gene expression include chemicals such as benzanthracene (BA), dimethyl benzanthracene (DMBA) or 5-azacytidine. Alternatively, treatment may also comprise altered conditions such as hypoxia which involves subjecting a cell to a reduced oxygen content, exposable to radiation or other stresses to the cell.

The host animal is preferably the same species as the cell to be implanted. In cases of xenogeneic transplants, the host may be immunocompromised by genetically or by treatment with drugs such as immunosuppressants. A host may be immunocompromised genetically by breeding such as with nude mice or severe combined immunodeficient (SCID) mice. A host may also be immunocompromised by chemical or irradiation methods. An additional route to immunocompromise a host is to use transgenic technology to introduce an immunosuppressing gene or to introduce a foreign antigen gene. An immunosuppressing gene is a gene that affects the efficiency of the immune system such as a gene which inhibits the formation of cells of the B cell or T cell lineage. A foreign antigen gene, when expressed may cause the host to tolerate the antigens in a xenogeneic transplant and not mount an immune response.

The preferred site for reimplantation, the primary site, may be any site receptive to implantation. Some sites are preferred for implantation purposes such as the renal capsule, the testes, the prostate and the ovaries. A number of reasons may exist for choosing a site that they may include ease of implant, similar tissue type, immunoprivileged position and ease of inspection. Metastasises may migrate from the primary tumor to any secondary site on an animal including the usual sites consisting of lung, kidney, liver, lymph nodes, testis, spleen, ovaries and mammary. To avoid histocompatibility problems, the implant may be placed into a histocompatible host animal. Such problems are generally avoided if the host animal is syngenic. Alternatively, a non-histocompatible host may be used if the host can be made immunotolerant. Immunotolerant hosts may be a transgenic animal, or an immunocompromised animal. Immunocompromised animals may be derived from established mouse lines such as nude mice of severe combined immune deficiency (SCID) mice, or by laboratory treatments such as radiation, chemical, transgenic treatment, pharmaceutical or genetic targeting. Hosts may also be transgenic or immunocompromised animals or genetically matched to the mammalian cells to be introduced. Sufficiently immunosuppressed animals can be made tolerant to xenogeneic transplants.

After implantation the host animal is maintained under normal conditions to develop metastases. Alternatively, the host animal may be subjected to an altered treatment or environmental condition to stimulate or repress metastasis or induce other cellular functions. In metastasis, a subpopulation of cells of the implantation site invade and establish one or more secondary colonies in the host animal. The behavior of the implanted cell will depend on the cell type, the transfected sequence and the implantation location. Typical secondary sites for metastatic colonies include lung, kidney, liver, lymph nodes, brain, testis, spleen, bone, ovary, skin and mammary tissue. Metastatic development times vary from days to weeks even months. Cells with a high metastatic potential tend to progress to metastasis quickly while cells with a low metastatic potential may require very long periods of time that span significant portions of the life span of the animal.

The host animal may be analyzed for metastatic development weekly, from one week to 20 weeks to six months, nine months or one year after implantation. For animals with longer life spans such as sheep, the animal may be inspected yearly from one year on up to ten years for metastatic tumors. Metastases can be detected by examinations such as palpation, biopsy, imaging, exploratory surgery, CAT scans, autopsy, X-ray and direct observation. In addition, tissue samples may be taken surgically from the host mammal and subjected to histological or other examination for the detection of metastases.

Expressed sequences include mRNA, rRNA, hnRNA, DNA, cDNA and any nucleic acid sequence that is expressed in the cell. These sequences may be amplified by in situ techniques or by purification of nucleic acid from collected cells. Expressed sequences may be obtained by extracting nucleic acids from cells before implantation, at the primary site or at the secondary site. Cells collected at these sites may optionally be cultured for a time before nucleic acid extraction. The effects of treatment with gene expression modifying agents or environmental conditions can be ascertained by collecting cells before and after treatment. Treatment may be applied to the cells while the cells are in the host mammal or after the cells are excised and in culture. Nucleic acids are collected from cells using techniques that are well known to those of ordinary skill in the art.

Expressed sequences may be used directly for polymerase chain reaction (PCR) analysis using, for example, the technique of reverse transcriptase polymerase chain reaction (RT-PCR). Alternatively, RNA may be enriched for mRNA using a poly-A RNA enrichment method. Numerous poly-A RNA enrichment methods exist and are commercially available. Techniques used for poly-A RNA enrichment include oligo-dT columns, oligo-dT magnetic beads, and oligo-dT cellulose. RNA may be further processed into cDNA before analysis by reverse transcription using reverse transcriptase. The cells or the extracted nucleic acid may be preserved, such as by freezing, and analyzed at a later time.

Differential display polymerase chain reactions (DD-PCR) are performed on the expressed sequences using two variable primers which may contain the same or entirely different sequences or an anchor primer and a variable primer. If an anchor primer is used, one anchor primer and one variable primer create a single or a single set of reaction products for each reaction. A complete profile may include 25 or more different PCR reactions per sample wherein each PCR reaction is performed with the same anchor primer and a different variable primer. DD-PCR may also be performed using anchor and variable primers which contain the same sequence. Whether a particular reaction is used depends on whether a difference exists between the products of two PCR reactions using the same primers. When a significant difference exists between the expression sequences amplified, one pair of PCR reactions may be sufficient and informative.

Anchor primers are preferably oligonucleotides with a poly-T sequence at the 5' terminals and a dinucleotide selected from the group consisting of AA, AG, AC, AT, GA, GG, GC, GT, CA, CG, CC and CT at the 3' terminals. The length of the poly-T sequence is typically between about five to about 30 bases in length and preferably between about ten to about twenty nucleotides in length. The total length of the anchor primer can vary greatly for each experiment but is preferably between about seven to about 32 and more preferably between about twelve and about 22. Differential diagnostic polymerase chain reaction may also be performed using an anchor primer of any sequence and a length between about five to about 30, preferably between about five to about 20 and more preferably between about seven to about 12 bases. The variable primer may comprise a random sequence, or a specific sequence. Variable primers preferably are oligonucleotides with a length between about five to about 30, preferably between about five to about 20, and more preferably between about seven to about twelve bases in length.

To enhance detection of the PCR product, the anchor primer or the variable primer or both may comprise a detectable moiety. Examples of detectable moieties include radioactive moieties, phosphorescent moieties, magnetic moieties, luminescent moieties, conjugatable moieties or other detectable moiety. A plurality of detectable moieties may be used to enhance detection or to simplify data analysis. Other detectable moieties include conjugatable moieties and molecules which can bind specifically to other molecules which are themselves detectable. Examples of conjugatable moieties include avidin, streptavidin, biotin, antibody, antigen, cell adhesion molecules and other molecules with similar activities.

Detectable moieties are preferably labeled nucleotides. A nucleotide may be any natural or synthetic nucleotide or nucleotide analog capable of incorporation into an elongation reaction in a polymerase chain reaction. Labeled nucleotides include nucleotide triphosphates labeled with one or more radioactive atoms such as $^{32}P$, $^{33}P$, $^{3}H$, $^{14}C$, $^{125}I$ and $^{35}S$.

Products of the DD-PCR reactions are compared to detect the metastatic sequences. A dominate metastatic gene product is expected to be present in a metastatic tumor while a recessive metastatic gene product is present in a non-metastatic tumor. Comparisons can be performed between expressed sequences from cells at secondary sites with cells at any stage in the method, including untreated, transfected or treated mammalian cells, implanted cells, or cells from the primary site in the host animal. DD-PCR products may be analyzed by any method which reliably compares the products of two polymerase chain reactions. Typical analytical methods used for this purpose include polyacrylamide gel electrophoresis, capillary electrophoresis and high pressure liquid chromatography (HPLC). Product produced from DD-PCR may be analyzed in double-stranded form or single-stranded form. When the products of the DD-PCR reaction are labeled the sizes and distribution of the products may be monitored and analyzed by following the labels using a radiation monitor or by autoradiography. For example, DD-PCR performed in the presence of radioactive primers or nucleotide triphosphates can be analyzed by gel electrophoresis, by capillary electrophoresis, or by HPLC. Products are easily monitored by the presence of radioactivity.

Another method for analyzing and isolating metastatic sequences is to sequence the amplified nucleic acid sequences. Sequencing may be performed using standard methods well known to those of ordinary skill in the art. The resulting sequence may be compared to a sequence database created or well-known, such as Genbank, for identification or for locating homologs. The sequencing information may be used to calculate the physical characteristics of the nucleic acids such as melting temperature and secondary structure. The primary sequence and the physical characteristic may be used to synthesize optimal nucleic acid probes for the detection or staging of metastasis or conditions that are predictive of the presence or absence of the metastatic condition.

Another embodiment of the invention is directed to a method for identifying a metastatic sequence. A mammalian cell is pretreated with a metastatic agent to form a population of cells predisposed to metastasize. The treated cells are introduced into a host mammal at a primary site. The host animal is maintained for a period of time sufficient to develop a metastasis at a secondary site. Expressed sequences of cells at the primary site and cells at the secondary site are treated with a genotoxic agent or subjected to genotoxic conditions. Expressed sequences of the treated cells are amplified by differential display polymerase chain reaction and compared with untreated cells from any previous step to identify the metastasis sequence.

The metastatic agent may be a chemical compound, a nucleic acid or a protein that alters the metastatic potential of a cell or relates to or is associated with the metastatic process. Chemical compounds include retinoids such as 4-hydroxyphenyl (4HP). Other agents include the proteins TGF-β1, Cyclin D1, p21, p34, p53, lysyl oxidase, caveolin, actin binding protein, ubiquitin activating enzyme E1, nmb or α-actinin 3, or their respective genes. The metastatic agent may be a metastatic stimulant or a metastatic suppressant. Metastatic stimulants may be used to enhance the sensitivity of the metastasis sequence detection method. Conversely metastatic suppressants may be used to decrease the sensitivity of the method enabling the selective identification of potent metastatic sequences or sequences specific to a particular tissue type or metastatic disorder. Treatment may comprise direct contact with the metastatic agent or incubation for a period of time. Metastatic agents enhance the metastatic potential of the implanted cells and increase the sensitivity and the speed of the overall method.

The cells at the primary site and the metastatic cells at the secondary site may be treated with a genotoxic agent in vivo or in vitro. In vivo treatment may comprise injecting genotoxic agents directly into the host mammal or specifically applying the agent with, for example, topical formulations. The cells at the primary site and the secondary site may also be isolated from the host animal and treated with the genotoxic agent in culture. Genotoxic agents are chemical compounds, nucleic acids or proteins that alter gene expression by affecting the nucleic acid genome directly by, for example, chemical modification, or indirectly by, for example, altering components associated with gene expression. Such agents include, for example, benzanthracene (BA), dimethyl benzanthracene (DMBA) and 5-azacytidine, and may include metastatic agents as well. In addition to or in place of genotoxic agents, the cells may be treated to hypoxic conditions or radiation to alter gene expression. Metastatic sequences identified in these methods may be specific for particular genotoxic agents or conditions.

Another embodiment of the invention is directed to the use of a host animal with an altered genotypic or phenotypic predisposition for metastases. A host animal may be screened for endogenous expression of a metastasis gene. Particularly useful metastatic sequences include TGF-β. A host animal with reduced levels of a metastatic gene product may be used to isolate novel metastatic genes. Host animals may be screened for reduced levels of metastatic gene expression. In addition, transgenic technology may be used to ablate a metastatic gene in the germline of a host animal.

The function of the metastatic sequences identified by the methods of the invention may be ascertained through differential expression pattern. For example, a dominant metastatic gene will be present in a metastatic cell while a recessive metastatic gene is present in a non-metastatic cell. Metastatic sequences may be detected as bands which are present in the DD-PCR of metastases isolated in secondary sites and absent from DD-PCR products of primary cells. These sequences may be dominant metastatic genes whose expression is directly responsible for metastasis, or they may be metastasis-associated genes whose expression correlates with metastasis. Either are useful for therapy and/or diagnosis. Conversely, DD-PCR bands which are present in primary site tumors, but absent in secondary metastatic sites, may be dominant metastasis suppression genes. Dominant metastasis suppression genes comprise genes whose expression suppresses metastasis while nonmetastatic genes comprise genes whose expression correlates with non-metastatic tissue. Genes which are highly correlative with either the metastatic phenotype or the non-metastatic phenotype may be isolated. Isolation can be performed by cutting the appropriate nucleic acid in the band of a polyacrylamide gel or by collecting the appropriate fraction in an HPLC or capillary electrophoresis. The nucleic acid may be cloned into a plasmid vector, and sequenced, or synthetically prepared.

Another embodiment of the invention is directed to a method for identifying sequences in a metastatic pathway which are responsive or unresponsive to extracellular signals. Such sequences may be used in therapy and diagnosis of metastatic disorders. Implanted cells or cells from a primary site and cells from a secondary site are treated with extracellular signals. RNA sequences from the treated cells are compared with RNA sequences of the untreated cells. Treated cells and untreated cells may be derived from a short term or long term in vitro culture of primary tumor and malignant tumors. Alternatively, a part of a primary tumor and a part of a malignant tumor may be collected before the animal is treated with an extracellular cytokine or other factor. Long term cultures, or cell lines of primary and malignant cells may also be used as recipients of extracellular growth signal treatment. Suitable signals for each experiment will depend on the cell type. Generally, growth factors, lymphokines, inhibitory factors, migratory factors or hormones may be used. Factors previously isolated by commercial or methods of the invention and factors associated with or causative or suppressive of metastasis are preferred. Thus, transforming growth factor β1 (TFG-β1) may be used to treat cells before DD-PCR analysis. Proteins encoded by the genes isolated by this method are especially useful for the treatment of cells for the isolation of additional sequences. The identification of one sequence responsive to the extracellular signal pathway allows for the identification of additional. genes upstream and downstream from that sequence.

Another embodiment of the invention is directed to metastatic sequences identified by the methods of the invention. Metastatic sequences are sequences associated with the presence or absence of a metastasis or related to the metastatic process. Metastatic sequences can be used in the therapeutic treatment of metastases. Metastatic-related sequences include dominant metastatic sequences, recessive metastatic sequences, metastasis-associated sequences, dominant oncogenes, recessive oncogenes and cell cycle genes. These genes encode, for example, proteins involved in cell cycle, signal processing, DNA replication, growth regulation, inter and intra cellular signaling transcription control and translation control.

Metastatic sequences identified by the methods of the invention were obtained by the following screens for metastatic sequences: (1) Met; (2) p53; and (3) TGF-β1. The screen designated Met was performed by comparing RNA extracted from a cell line established from a primary tumor and a cell line derived from an associated metastatic tumor-derived cell line. The screen designated p53 was a screen for dominant or recessive metastatic sequences in which cells of a murine prostate cancer cell line were infected with either an adenoviral vector expressing wild-type p53 or mock-stimulated with E1 deleted adenoviral vector prior to starting the screen. The TGF-β designation indicates that the cells were pre-treated with or without TGF-β prior to the step in the screen in which cellular RNA is extracted. Sequences isolated by the methods described herein are useful in the treatment and detection of metastasis and other disorders. Disorders which may be treated comprise both malignant or nonmalignant disorders. Examples of nonmalignant disorders include benign enlargement of the prostate, hyperplasia, such as nodular hyperplasia, hypertrophy, such as benign prostatic hypertrophy and dysplasia. Malignant disorders include prostate cancer, breast cancer and other non-benign cancers.

Another embodiment of the invention is directed to nucleic acids which comprise a sequence identified by the method of the invention such as, for example, caveolin, ABP280 (actin binding protein 280), lysyl oxidase, the gene encoding p99 (clone 99) and the nmb gene (clone 29). Nucleic acids comprising a sequence corresponding to any of these genes may be used in treatment of neoplastic disorders and malignant tumors, or in diagnostic kits for screening biological samples for the presence or absence of metastasis or metastatic potential. The nucleic acid may be DNA, RNA or PNA and may comprise additional sequences such as a promoter sequence for expression of a sense or antisense message, recombination sequences for gene targeting, selectable markers for transfections, or replication origins for passage in a prokaryotic or eukaryotic host such as animal cells, bacteria or yeast. Treatment may involve using the sequences in gene therapy, including gene ablation, gene expression and antisense suppression. Diagnosis may involve genotypic analysis of samples to determine the existence and expression levels of the expressed sequence.

Characterization of three metastatic sequences identified by the methods described herein reveal different expression patterns in metastatic cells. Also, two of these sequences were encoded for by known genes, while the third is the product of a novel gene. These expression patterns suggest that the genes encoding the metastatic sequences represent different classes of metastatic genes. One such gene, the lysysl oxidase gene, was found to be repressed in metastatic tissues as compared to expression levels in primary tumor or normal tissues, suggesting lysyl oxidase may function in a tumor suppressing pathway. Contrasting results were obtained for a second gene, the caveolin gene. Unlike lysyl oxidase, caveolin levels were found to be increased in metastatic tissues suggesting a role for caveolin in metastasis-associated processes.

A third metastatic sequence was identified and designated p99 (FIG. 1). This sequence contains the predicted peptide sequence of the p99 protein. A Northern blot of p99 expression in mouse normal prostate-derived, mouse prostate primary tumor-derived and mouse metastasis-derived cell lines showed that expression of p99 was found to be induced by the tumor suppressor p53 and, similar to caveolin levels, p99 levels were found to be up-regulated in metastatic prostate cells as compared to primary tumor-derived cells and cells from normal prostate tissue.

Although p99 has not previously been associated with metastasis, the deduced amino acid sequence of p99 shares up to 44% homology with several members of the epithelial membrane protein family having four transmembrane domains. Northern blot analysis show up-regulation of p99 in response to gamma radiation and DNA damaging agents in a p53-dependent manner with relatively high expression in mouse urogential tissues including prostate, bladder, kidney and seminal versicles. In addition, high p99 p53-dependent expression levels were detected in liver, colon and heart. Expression of p99 as an N-terminal. fusion protein with EGFP demonstrates perinuclear localization of the fusion protein, with accumulation in the endoplasmic reticulum and Golgi apparatus. FIGS. 2–8 summarize the isolation and characterization of metastatic sequences identified using the herein. described methods.

Specifically, FIG. 2 contains a compilation of the sequences obtained using the described methods for identifying dominant and recessive metastatic sequences. The following information is provided in FIG. 2 for each clone the name/number of the clone, the length of the clone, the degenerate oligonucleotide primer used in the differential display PCR, and the type of screen—Met, p53 or TGF-β-from which the clone was derived.

The screen designated Met was performed by comparing RNA extracted from a cell line established from a primary tumor and a cell line derived from metastatic cells. The screen designated p53 was a screen for dominant or recessive metastatic sequences in which cells of a murine prostate cancer cell line were infected with either an adenoviral vector expressing wild-type p53 or mock-stimulated with E1 deleted adenoviral vector prior to starting the screen. 148-1 cells are p53 null and carry integrated retrovirally expressed ras and myc oncogenes in their genome. The TGF-β designation indicates that the cells were pre-treated with or without TGF-β prior to the step in the screen in which cellular RNA is extracted.

FIG. 3 contains data obtained through the initial characterization of some of the sequences resulting from the Met screen. The following data, as available, is shown in FIG. 3: the name/number of the clone, the cell line from which the clone was derived; the degenerate oligonucleotide primer used in the differential display (DD) polymerase chain reaction (PCR), size of the DD-PCR product, the most homologous murine gene or sequence, the most homologous human gene or sequence, whether the clone is transcriptionally up- or down-regulated in the indicated cell line as determined by Northern Blot analysis, and whether the clone is transcriptionally up- or down-regulated.

FIG. 4 contains data obtained through the initial characterization of some of the sequences (also) resulting from the Met screen. The following data, as avalilable, is provided in FIG. 4: the primer used in the DD-PCR and the size of the resulting product, the most homologous murine gene or sequence, the most homologous human gene or sequence, whether the clone is transcriptionally up- or down-regulated in the indicated cell line as determined by Northern Blot analysis.

FIG. 5 contains data obtained through the initial characterization of some of the sequences (also) resulting from the Met screen. The following data, as available, is provided in FIG. 5: the primer used in the DD-PCR and the size of the resulting product, the most homologous murine gene or sequence, the most homologous human gene or sequence, whether or not the clone is transcriptionally up- or down-regulated in the indicated cell line and performed in duplicate (screen 1 and screen 2).

FIG. 6 contains data obtained through the initial characterization of some of the sequences (also) resulting from the p53 screen. The following data, as available, is provided in FIG. 6: the primer used in the DD-PCR and the size of the resulting product, the most homologous murine gene or sequence, the most homologous human gene or sequence, whether or not the clone is transcriptionally up- or down-regulated in the indicated cell line as a result of a p53 expression after 12 (+12) or 24 (+24) hours and performed in duplicate (screen 1 and screen 2).

FIG. 7 contains data obtained through the initial characterization of some of the sequences (also) resulting from the TGF-β screen. The following data, as available, is provided in FIG. 7: the primer used in the DD-PCR and the size of the resulting product, the most homologous murine gene or sequence, the most homologous human gene or sequence, whether or not the clone is transcriptionally up- or down-regulated in the indicated cell line as a result of a 12 hour treatment/exposure to TGF-β and performed in duplicate (screen 1 and screen 2).

FIG. 8 contains data obtained through the initial characterization of some of the sequences resulting from screening a phage library. The following data, as available, is provided in FIG. 8: the primer used in the DD-PCR and the size of the resulting product, the most homologous murine gene or sequence, the most homologous human gene or sequence, whether or not the clone is transcriptionally up- or down-regulated in the indicated cell line and performed in triplicate (screen 1, screen 2 and screen 3), and the number of the positive plaques obtained in the phage screen.

The sequences identified by the methods of the invention have numerous potential applications. For example, one embodiment of the invention is directed to methods for treating a neoplastic disorder comprising administering a pharmaceutically effective amount of composition containing a nucleic acid having a sequence identified according to the methods of this invention, its expression product or fragments of either. The nucleic acid may be in the form of a sense or anti-sense single-stranded or double-stranded nucleic acid. The nucleic acid may be administered by injection, pulmonary absorption, or topical application and delayed release. The nucleic acid may be combined with a pharmaceutically acceptable carrier such as water, alcohols, salts, oils, fatty acids, saccharides, polysaccharides administered by injection, pulmonary absorption, topical application or delayed release. More than one carrier may be used together to create a pharmaceutical with desirable properties.

Treatment may involve gene replacement, gene targeting, anti-sense inhibition, gene expression or gene suppression. Gene replacement involves replacing a copy of a defective gene with another copy by homologous recombination. Gene targeting involves the disruption of a cellular copy of a gene by homologous recombination. Anti-sense inhibition exploits the specificity of hybridization reactions between two complementary nucleic acid chains to suppress gene expression. Cloned genes can be engineered to express RNA from only one or the other DNA strands. The resultant nucleic acid, which may be DNA, RNA or PNA, or another synthetic sequence, hybridizes to the sense RNA and inhibits gene expression. Gene expression and gene suppression involve the introduction of genes whose expression actively inhibits neoplastic transformation and metastasis.

Another embodiment of the invention is directed to a kit or diagnostic aid useful for screening biological samples for detection of metastasis, neoplasia or for the staging of a tumor comprising sequences isolated according to the methods of the invention. Kits contain nucleic acid such as DNA or PNA of a sequence that hybridizes (or fail to hybridize for example with competition assays) to metastatic-specific sequences in a biological sample. Hybridization may be detected using conventional detection reagents and methods well known to those of ordinary skill in the art. The kit further comprises reagents and materials useful in such kits, such as, for example, buffers, salts, preservatives, and carriers, all of which are well known to those of ordinary skill in the art. Such kits are useful for the analysis of biological samples containing fluids and/or tissues to screen for the determination of normal nonmalignant, neoplastic or malignant cells. Kits may comprise additional reagents useful for the extraction of nucleic acids from a tissue sample. Reagents for analyzing the nucleic acid extracted from a tissue sample such as polymerase chain reaction reagents and Southern blot reagents may also be included.

Correlation of Caveolin Expression with Neoplastic Disorders

One of the gene products found to be associated with metastasis in the mouse model as well as in human prostate cancer is caveolin, a major structural component of an organelle termed caveolae. Caveolin is an integral membrane protein and a principal component of caveolae. Caveolae are small invaginations at or near the plasma membrane of most smooth muscle cells. Caveolin was initially identified as a major v-src substrate for phosphorylation in Rous sarcoma virus transformed chicken embryo fibroblasts (Glenney, J. R., J. Biol. Chem. 264, 10163–20166, 1989). Recent studies suggest that caveolae may function in some capacity as a component of specific signal transduction pathways. In the only published report which documents caveolin expression in non-transformed and transformed cells, it was demonstrated that both caveolin expression as well as caveolae are lost during transformation of NIH-3T3 cells by v-abl, bcr-abl, middle T antigen and activated ras (Koleske, A. J., Baltimore, D. and Lisanti, M. P. Proc. Natl. Acad. Sci., USA 92, 1381–1385, 1995).

The association of caveolin with metastasis has been confirmed in animal models and in human prostate and breast cancer that increased levels of the caveolin protein are associated with metastasis (Yang, G. et al., Clin. Can. R. 4:1873–1880, 1998). Thus, the identification of caveoli as a metastatic sequence provides another example validating the importance of the selected animal model since many discoveries made using this model have also been found to be relevant to human prostate cancer (Truong LD, et al., *Hum. Pathol.* 24:4–9, 1993; Thompson T C, et al., *J. Cell. Biochem.* 16(S):54–61, 1992; Eastham J A, et al., *Lab Invest.* 73:628–635, 1995; Williams R H, et al., Clin. *Cancer Res.* 2:635–640, 1996; Eastham J, et al., *Clin. Cancer Res.* 1:111–1118, 1995; Yang G, et al. *Clin. Cancer Res.* 2:635–640, 1996; Stapleton AMF, et al., *Clin. Cancer Res.* 3:1389–1397, 1997; Aihara M, et al., *Hum. Pathol.* 25:797–801, 1994; Aihara M, et al., *Cancer* 75:522–529, 1995; Yang G, et al., *Cancer* 78:1267–1271, 1996).

The subsequent production of stably selected clones with antisense caveolin resulted in a significant reduction in metastatic activities relative to vector-control clones and parent cell lines. Surprisingly, it has been discovered that tumors produced by the antisense caveolin clones significantly regressed in response to surgical castration in vivo. Eleven days following androgen ablation, tumors derived from three independent antisense clones regressed by approximately 30% relative to the wet weights produced in either vector-control clones or parental clones which did not respond to castration therapy under the same conditions. The antisense caveolin tumors that responded to castration therapy also demonstrated significantly increased levels of apoptosis relative to either vector-control clones or parental cell lines. The data indicates that reduction of caveolin levels not only suppresses metastatic activity, but also restores androgen sensitivity. Thus, caveolin-1 is a metastasis-related gene as well as a candidate androgen resistance gene for prostate cancer in man. Caveolin-2 forms a heterodimer with caveolin-1 and is also expected to be useful in the invention. Caveolin-3 is specifically expressed in muscle cells and may be useful for certain types of metastatic disorders and not others. These results are believed to establish a new paradigm for understanding androgen refractory disease and open the door for new innovations in prostate cancer therapy.

Surprisingly, caveolin expression increases in metastatic human prostate cells as compared to human primary prostate tumors. The general observation that caveolin mRNA and protein levels are consistently elevated in metastatic prostate cancer compared to non-metastatic prostate cancer in both mouse and human prostate cancer models is different from the caveolin gene transfer results in NIH-3T3 cells. However the difference may be attributed to the difference in the underlying mechanism of transformation to tumorigenicity (soft agar assay) in NIH-3T3 cells compared with those involved in carcinogenesis/metastasis in vivo using the mouse prostate reconstitution model system.

As caveolin expression correlates with metastasis, application of biological-technologies designed to block the activity of caveolin or the function of caveolae may have therapeutic benefits for the treatment of neoplastic disorders such as human prostate tumors. Specific treatment approaches using caveolin may include the delivery of antisense or dominant negative caveolin sequences using expression or viral vectors, as well as the use of specific anti-caveolin antibodies. As the caveolin gene is expressed specifically in metastatic cells, the gene promoter (as well as the promoter of other metastatic-specific genes such as p99 {which is selectively expressed in metastatic cells} and lysyl oxidase {which is selectively suppressed in metastatic cells}) may also be specifically induced in metastatic cells. Thus, by functionally incorporating into normal cells a gene encoding a toxic product downstream of the caveolin promoter, metastatic disease should not develop because when and if it does, the toxic product is expressed and the cells expressing it are destroyed. This has been shown for the caveolin-1 promoter and is believed to be true for the caveolin-2 and caveolin-3 promoters as well as other metastatic-specific genes. It is well known to those of ordinary skill in the art how to create genetic constructs that take advantage of selective expression, or the lack thereof, in metastatic cells for the treatment and prevention of metastatic disease.

Additional approaches could also target the caveolae, but are not specifically based on caveolin function. Additional protein and non-protein components of caveolae could also be targeted for abrogation or the local or systemic administration of a nutritional or biological agent may also be used. For example, caveolae are extremely rich in cholesterol and disruption or depletion of this molecule may alter the function of caveolae.

Multiple genetic activities are involved in androgen ablation-induced prostate regression, yet very little is known regarding the rate limiting steps in the molecular cascade that leads to regression, or the molecular basis of hormone resistance in prostate cancer. A mouse model has been developed to identify metastasis-related genes in prostate cancer. This model includes a series of clonal cell lines derived from prostate cancer metastases that developed in vivo using the mouse prostate reconstitution (MPR) model system.

Specifically, panels of clonal cell lines were derived from primary prostate tumors as well as metastases from the same animal using the MPR mouse model system for prostate cancer metastasis. Within this panel of cell lines, there are sets that are both genetically and biologically matched such that the primary genetic difference between these cell lines should be related to metastatic activities. This is made possible, in part, by unique retroviral integration sites that serve as markers for clonality. Using a modified differential display-polymerase chain reaction (DD-PCR) approach, numerous genes were identified that are related to metastasis in human prostate cancer. For example, the caveolin gene was found to be up-regulated in metastasis-derived cells relative to their primary tumor-derived counterparts. (Yang, G. et al., Clin. Can. R. 4:1873–1880, 1998). The caveolin gene, first identified as the major phospho-protein in src transformed cells (Glenney J R, J. Biol. Chem. 264:20163–20166, 1989), was shown to be the major structural component of caveolae. (Lisanti M P, et al., Mol. Memb. Biol. 12:121–124, 1995). Caveolae are membrane domains which may compartmentalize some single transduction pathways, and recent identification of an integrin/urokinase plasminogen activator receptor (uPAR)/caveolin complex (Wei Y, et al., Science 273:1551–1555, 1996) provides a mechanistic framework for linking alterations of caveolin expression with two potentially important properties of malignant progression of metastasis-integrin mediated cell-cell adhesion and uPAR mediated proteolytic activity. With commercially available antiserum to caveolin, increased protein levels in both mouse and human prostate metastases have been confirmed. (Yang, G. et al., Clin. Can. R. 4:1873–1880, 1998). Further, the expression of caveolin in three mouse metastatic cell lines has been experimentally suppressed by expression of an antisense cDNA construct. Suppression of caveolin does not reduce the growth potential of mouse prostate cancer cells, but does reduce both the incidence of metastatic spread and the actual tumor volume of lymph node metastases: (Yang, G. et al., Clin. Can. R. 4:1873–1880, 1998).

Surprisingly, it has been discovered that the antisense caveolin clones have also acquired hormone sensitivity. Orthotopic tumors that form from antisense caveolin clones, but not vector-control clones or parental cells, regress by approximately 30% in wet weight following surgical castration. Further studies confirm increased levels of apoptosis in antisense caveolin tumors relative to non-regressing control tumors. Continuous massaging of three antisense caveolin tumors in castrated male hosts resulted in increased caveolin protein levels. This data indicates that caveolin alone is responsible, in part, for the development of hormone-refractory prostate cancer in the present model system. These novel results should have a significant impact on prostate cancer by: 1) spawning additional investigations that will reveal the molecular pathway leading from the androgen ablation stimulus to regression of prostate cancer in vivo; 2) leading to a more complete understanding of the molecular basis of hormone-refractory prostate cancer; and 3) ultimately leading to the development of anti-metastasis therapy based on small molecule, immunological or gene therapy approaches. Future studies will likely result in tremendous therapeutic impact on men in that suppression of caveolin or other molecules in the caveolin-androgen resistance pathway will lead to effective anti-metastasis therapy.

As noted, an animal model has been developed for experimental prostate cancer research, the mouse prostate reconstitution (MPR) model. (Thompson, T C, et al., Cell 56:917–930, 1989). A unique and significant feature of this "transgenic gland" model is that by manipulating the number and types of initiating genetic events, it can be used to produce and study every step of carcinogenesis, from pre-malignant changes through the metastatic cascade. (Thompson T C, et al., *Mol. Carcinog.* 7:165–179, 1993; Thompson T C, et al., *Oncogene* 10:869–879, 1995). Experiments using the MPR model have also provided numerous cell lines that have been utilized extensively for both in vitro and in vivo studies. Significant advances in understanding prostate cancer metastasis have come from analyzing cell lines that were derived from either a primary tumor or a tumor at a metastatic site. Since the tumors are initiated as a result of retroviral infection, primary tumor- and metastasis-derived cells from the same animals are clonally related and may be compared, based on unique retrovirus integration sites. Differential display PCR has been adapted and refined to compare mRNA from clonally matched cell lines and identify numerous genes whose expression appears to be metastasis specific.

Surprisingly, it has been discovered that when tumor-bearing animals are castrated following orthotopic injection of metastatic cell lines with antisense caveolin (ABAC3, ABAC5, and BACS4) tumor volume is reduced relative to sham surgery-treated animals or castrated animals that received a testosterone implant. For example, antisense caveolin has been shown to restore androgen sensitivity in 3 independent cell lines. Orthotopic tumors were initiated by injecting 5000 cells into the dorsal prostate of 129 male mice. Three days later the animals were castrated (cast) or sham operated. Some animals also received implants of silastic tubing containing testosterone proprionate (cast+T) or an empty pellet (cast EP). Tumor volume was determined after 2 weeks. All values for ABAC3, ABAC5, and BACS4 in the cast and cast EP groups are significantly different from cast+T pellet and sham controls ($p<0.05$).

In contrast to the antisense tumors, two parental cell lines (148-1LMD and 151-2LMC), as well as control vector only clones (ABH11, ABH14 and BHS3) did not respond to androgen withdrawal. Significantly increased apoptosis is believed responsible, in part, for the regression, and that in addition to growth suppression, a reduction in metastasis also occurs following castration only in the antisense clones.

The model system has been generated based on the finding that high caveolin levels block castration-induced prostatic regression, and reduction in caveolin levels appear to release this block. This model is believed to normalize the nonrelevant androgenic-stimulated gene activities. This model system involves clonal cell lines in which caveolin levels have been selectively reduced by stable antisense caveolin transfection as well as the production of clonal vector control cell lines. When these cell lines are injected orthotopically in vivo, allowed to produce tumors (that are of equivalent size at 3 days post inoculation), and subjected to hormone manipulation, only the antisense caveolin stable clones undergo castration-induced regression, whereas the vector control clones and their parental cells do not. Therefore, in this model system, the gene activities that are not directly involved with castration-induced regression, but are induced or repressed following the castration stimulus, should be present in both vector control clones as well as antisense caveolin clones. The only differences in the gene activities between the two groups of cell clones in response to the castration stimulus should be related to castration-induced regression which occurs only in the antisense caveolin clones.

During normal development, the mouse prostate undergoes extensive growth and morphogenesis in response to androgenic steroids (Cunha G R, et al., *J. Androl* 13:465–475, 1992). Preliminary data indicates that overexpression of caveolin can block castration-induced regression of mouse prostate cancer. Therefore, it seems likely that overexpression of caveolin would block the normal testosterone-stimulated growth and development of mouse prostate. Growth and development that occurs in prostatic tissue in the mouse is not only dependent on increasing testosterone concentrations that occur with reproductive maturity, but also fluctuations in testosterone that occur shortly after birth (Cunha G R, et. al., *J. Androl* 13:465–475, 1992). It is believed that under the influence of caveolin overexpression, a normal mouse prostate would be insensitive to such changes and an aberrant phenotype would be produced.

One embodiment of the invention is directed to the caveolin gene and caveolin protein, or portions thereof, in the treatment of neoplastic disorders and preferably metastatic disease such as, for example, metastatic prostate cancer. Treatment involves administration of the sequence of the gene, which may comprise only the promoter region and a toxic gene to a patient to destroy metastatic cells.

Therapies for prostate cancer metastasis become apparent to those of ordinary skill in the art from an increased understanding of the molecular mechanisms of cancer progression. Preliminary data indicates that overexpression of caveolin blocks the castration-induced pathway that leads to apoptosis-mediated regression of mouse prostate cancer in vivo. One possible explanation is that the caveolin protein is binding inducible nitric oxide synthase and inhibiting activity following an initial castration-induced stimulus (Chamness S L, et al., *Fertil. Steril.* 63:1101–1107, 1995). Therefore, reduction of caveolin levels in human prostate cancer prior to androgen ablation therapy would likely convert it from androgen-insensitive to androgen-sensitive and result in increased tumor regression. The present invention relates to methods for producing significant reductions in caveolin protein prior to androgen ablation therapy. The molecular tools for applying anti-caveolin therapy include recombinant viral vector systems (such as recombinant vectors derived from retro viruses, herpes viruses, lentiviruses, adenoviruses, adeno-associated viruses and T cell leukemia viruses such as HTLV), antisense oligonucleotides, and small molecule and antibody interference.

Another embodiment of the invention is directed to the production of a transgenic mouse over expressing caveolin. In a preferred embodiment, caveolin expression is under the transcriptional control of the MMTV or the probasin promoter and is targeted for expression in the prostate gland. Transgenic mouse model systems have thus far proved to be invaluable tools for understanding gene functions within a complex biological milieu in vivo. Over the past 10 years hundreds if not thousands of transgenic mice have been generated and used to unravel the phenotypic effects of tissue-specific gene expression within the context of normal gene activities, i.e. normal mouse development in vivo. A transgenic mouse with targeted expression of caveolin to the prostate gland may result in overgrowth and abnormal differentiation of the mouse prostate in vivo. During development, the mouse prostate is exquisitely sensitive to changes in circulating androgen levels. Aberrant expression of caveolin will block the response to androgenic stimuli to a great extent, and prostatic epithelium in male caveolin-transgene mice will be deregulated for growth and differentiation. Analyses of these mice can be used to determine the extent of developmental abnormalities and pathological changes that occur. Hormone manipulation of these mice can provide insights into prostatic growth, morphogenesis and therapeutic efficacy in vivo. The caveolin transgenic mouse model is expected to provide significant and important information regarding the impact of overexpression of caveolin on normal mouse prostatic development as well as the possible pathological consequences of this gene activity.

Another embodiment of the invention is directed to significantly reducing caveolin levels (which may be caveolin-1, -2, -3 or combinations thereof) using specific gene-based technologies to result in reacquisition of sensitivity to castration in hormone-refractory mouse and human prostate cancer. In a preferred embodiment, recombinant adenoviral vectors may be used to over express antisense caveolin directly in mouse prostate cancer cells, thereby reducing caveolin levels. In a preferred embodiment, treatment with antisense caveolin adenovirus is combined with subsequent castration therapy to result in enhanced sensitivity of prostatic tumors to the stimulus and, therefore, more widespread apoptosis in cancer cells. Such therapy has direct application to human disease.

Another embodiment of the invention is directed to potentiation of androgen ablation therapy by reduction of caveolin protein using adenoviral vector systems, antisense oligonucleotides, antisense retroviral vectors, small molecules that interact with caveolin function and antibodies. For example, caveolin is involved in molecular transport and cell-cell interactions. Interference with these functional properties may interfere with metastatic development. Accordingly, caveolin-mimics (i.e. agents that mimic caveolin function) as well as mimics of other metastatic-specific functions can be used to treat and/or prevent metastatic disease. Optimal methodologies may be selected for the coupling of these therapies with surgical castration in an attempt to produce more widespread cell death in mouse prostate cancer.

Another embodiment of the invention is directed to methods to determine the molecular pathways of castration-induced regression in mouse prostate, cancer vis-á-vis the caveolin overexpression model system by, inter alia, assessment of specific apoptotic activities and gene activities previously shown to accompany castration-induced regression in both rodent and human model systems. In addition, differential display (DD)-PCR may be used to identify specific gene activities that are directly related to castration-induced regression using the unique model system of the present invention and ultimately, specific signal transduction pathways may be tested.

Reduced Lysyl Oxidase mRNA Levels in Metastatic Prostate Cancer

Previous studies indicate that acquisition of differential responses to transforming growth factor β1 (TGF-β1) by specific cell clones within a primary tumor can result in phenotypic traits that facilitate cancer progression or tumor metastasis in those cells. Cells of lung metastases-derived cell lines have been shown to secrete relatively large amounts of total TGF-βs, and to lack most or all TGF-β1-induced growth inhibition, yet retain the ability to respond to TGF-β1 as indicated by TGF-β1-induced expression of type IV collagenase matrix metalloproteinase-9. In contrast, cell lines derived from primary lung tumors were found to secrete relatively smaller amounts of total TGF-βs and retain TGF-β1-induced collagenase activity (Sehgal L, et al., Cancer Research 56:3359–3365, 1996). TGF-β1 has also been identified in association with prostate cancer (Truong L D, et al., Human Path.24:4–9, 1993; Eastham J A, et al., Laboratory Invest. 5:628–635, 1995). Thus, a correlation can be drawn between increased TGF-β1 expression and increased cancer progression.

Another embodiment of the invention is directed to the identification of genes that serve as downstream targets of TGF-β1 and may thus underlie the selective advantage of metastatic clones. To identify genes that are differentially induced or repressed by TGF-β1 treatment in association with prostate cancer progression, a strategy was utilized involving the use of a modified DD PCR technique (Liang P, et al., Cancer Res., 52:6966–6968, 1991; Liang P, et al., Science, 257:967–971, 1992; Ralph D, et al., Proc. Natl. Acad. Sci. USA, 90:10710–10714, 1993), and a panel of mouse prostate cancer cell lines derived from genetically matched primary tumor and metastasis. In the modification of the DD-PCR technique, the oligo (dT) primer was substituted with a semiarbitrary 10-mer for the initial reverse transcription and for subsequent amplification steps. Each primer amplifies a large number of primer-specific bands that are similarly expressed in either the presence or absence of TGF-β1, but in some cases, bands are induced or repressed in the 148-1PA cells by TGF-β1 stimulation.

The nucleotide sequence of the lysyl oxidase gene, a metastatic sequence, was also identified by the methods of the invention. A homology comparison between lysyl oxidase clones isolated by the invention and lysyl oxidase sequences entered in the GenBank database show a very close homology.

The approach used to identify TGF-β1-regulated genes involved establishing mouse prostate cancer cell lines, which were derived from primary tumors or metastatic deposits in the same host animal, implanted with a ras+myc-initiated p53-nullizygous MPR (Thompson, T C, et al., Oncogene, 10: 869–879, 1995). Multiple sets of early-passage clonal cell lines were established from both primary and metastatic tumor foci recovered from the same experimental animal. As the strains of mice used in these experiments are inbred strains and because conditions for outgrowth of both primary and metastasis-derived cell lines are closely controlled, resulting cell-line systems are both genetically and biologically matched. Therefore, the predominant genetic differences between the primary tumor-derived and metastasis-derived cell lines should be related to the metastatic process.

Cells of the primary mouse prostate cancer cell line, 148-1PA (Sehgal, L, et al., Cancer Res., 56:3359–3365, 1996), were either treated in vitro with 2 ng/ml TGF-β1 for 12 hours to induce TGF-β1-dependent gene expression, or left untreated for 12 hours prior to use in the modified DD-PCR protocol. DD-PCR was performed on RNA extracted from the TGF-β1 treated and untreated cells of primary tumor- versus metastases-derived cell lines. Cloned cDNA fragments were used to probe cellular RNA extracted from primary versus metastatic mouse prostate cancer cells for sequences that are differentially regulated by TGF-β1, using Northern blot analysis. Sequences that were found to be differentially regulated by TGF-β1 were used as probes to analyze constitutive gene expression by Northern blot analysis using a panel of primary and metastatic mouse prostate cancer cell lines. Numerous differentially regulated DD-PCR fragments were cloned, sequenced, and compared to mouse and human gene sequence databases. In approximately 90% of the cases, a portion of a known mouse gene or a mouse homologue for a human gene had been cloned. One of the cDNA fragments isolated by this approach was found to encode a portion of the mouse lysyl oxidase (LO) gene.

The detection of LO mRNA in the mouse prostate cancer cell line 148-1PA was demonstrated in a DD-PCR gel. 148-1PA cells were either treated with TGF-β1 (Lanes+) or left untreated (Lanes–) in serum free media (SFM), both for 12 hours, then DD-PCR was carried out using one of three different primers, P10, P11, or P12, as both the 5' and 3' primer. A TGF-β01-induced band was isolated, cloned and sequenced. Upon performing database (GenBank Version 86.0) searches with this sequence, the 307-bp fragment was found to be 100% identical (excluding three mismatched primer sequences) with the mouse LO gene and 93% identical with the human LO gene. The cloned LO fragment was then used in experiments with both the primary mouse prostate cancer cell line 148-1PA and its metastatic tumor-derived counterpart, 148-1LMD, to analyze and compare the extent of LO induction by TGF-β1.

A Northern blot analysis was performed on total RNA from the primary tumor-derived cell line 148-1PA and the lung metastasis-derived cell line 148-1LMD. Cells were either TGF-β1 treated, or left untreated, for both 12 and 24 hours in SFM. Induction of LO gene expression in 148-1PA cells was detected at both 12 and 24 hours after TGF-β1 treatment. In 148-1LMD cells, the constitutive level of LO was barely detectable, and no significant increase was observed as a result of TGF-β1-treatment. The blot was stripped and reprobed for PAI-1 gene expression. The PAI-1 gene is a TGF-β1-induced gene and encodes an extracellular matrix protein. PAI-1 gene expression has been reported to undergo stimulation to a similar extent in both primary tumor- and metastases-derived cell lines (Sehgal, L, et al., Cancer Research 56:3359–3365, 1996). Accordingly, PAI-1 expression was found to be induced by TGF-β1 to similar levels at both 12 and 24 hours in both 148-1PA and 148-1LMD cell lines. Equivalent RNA loading was verified by striping the blot and reprobing it with a rat glyceraldehyde 3-phosphate dehydrogenase (GAPDH) probe.

A Northern blot analysis was performed of total RNA from cell lines derived from primary tumors (148-1PA, 148-1PC 151-1PA, 151-1PB, 151-1PF and 151-2PA) and their genetically matched lung metastases (148-1LMA, 148-1LMC, 148-1LMD, 151-1LM1, 151-1LM2, 151-2LMA and 151-2LMC). These cell lines were derived from three independent animals (148-1, 151-1 and 151-2) (Thompson, T C, et.al., Oncogene, 10:869–879, 1995; Sehgal, L, et al., Cancer Res., 56:3359–3365, 1996) LO expression was readily detected in five of the six primary tumor-derived cell lines, and in only two of the seven lung metastasis-derived cell lines. Also, the expression of LO was significantly reduced in ras+myc-transformed NIH3T3 (3T3R/M) cells compared to parental NIH3T3 cells (3T3). The blot was stripped and reprobed with glyceraldehyde 3-phosphate dehydrogenase (GAPDH) as a control for RNA loading and transfer, and Endo B (cytokeratin 18), a marker for prostatic luminal epithelial cells, as a control for the epithelial origin of the cell lines (Thompson, T C, et al., Cell, 56:917–930, 1989). Endo B was present in all of the mouse prostate cancer cell lines documenting the epithelial origin of the cell lines. The GAPDH blot verified that RNA had been loaded equally in all lanes. Together, the results indicate that LO represents a TGF-β1-stimulated gene in nonmetastatic prostate cancer cells, but that during cancer progression, reduced LO expression becomes an acquired feature synonymous the metastatic phenotype.

In situ hybridization analyses were performed on LO expressed in mouse prostate tissues. To analyze mRNA levels in normal and malignant mouse prostate, the 307-bp LO fragment that was originally cloned by DD-PCR from 148-1PA cells was used for in situ hybridization analysis of normal, primary tumor, and metastatic mouse prostate cancer tissues. LO mRNA was detected predominantly in the epithelium and to a lesser extent in the stroma in normal mouse prostate. LO mRNA was detected predominantly in the epithelium and to a lesser extent in the stroma in primary mouse prostate cancer. LO mRNA was progressively less abundant in the lymph node metastasis associated with the primary tumor. The minimal background associated with this technique in which normal mouse prostate tissue was probed with an LO sense probe. The results indicate that significant mRNA levels are present in normal mouse prostate epithelium, and also in the stroma of normal mouse prostate albeit at a significantly reduced level. In the matched set of primary and metastatic mouse prostate cancer tissues, in situ hybridization analysis reveal significantly reduced levels of LO mRNA in primary mouse prostate cancer relative to normal mouse prostate epithelium and even further reduced levels of LO expression in the metastatic lesions.

In situ hybridization analysis was performed of LO expression in normal and malignant human prostate tissues. The 307-bp mouse LO DD-PCR fragment was utilized as a probe. This probe fragment is 93% homologous with the human LO gene and was, therefore, suitable for such studies. LO mRNA was abundant in benign glandular epithelium in human prostate. LO expression was markedly reduced in human prostate cancer. A further loss of LO mRNA signal was shown in lymph node metastatic disease. A control for background hybridization in which normal human prostate was probed with an LO sense probe to demonstrated the specificity of the analysis. The results of the in situ analysis of multiple normal and malignant human tissues revealed a pattern similar to that seen in the mouse. Significant levels of LO mRNA were detected in benign prostate epithelium. LO was also detected in normal prostatic stroma, but at a significantly reduced level. In primary human prostate cancer, LO mRNA levels were reduced relative to that seen in benign prostatic epithelium, and analysis of metastatic specimens revealed a further diminution of LO mRNA (Table 1).

TABLE 1

LO mRNA expression in normal prostate and prostate cancer relative LO mRNA levels in human prostate tissues were scored as negative (–) to strongly positive (+++), depending on the fluorescence intensity in tissue sections.

|  | $n^a$ | – | + | ++ | +++ |
| --- | --- | --- | --- | --- | --- |
| Normal stroma | 7 | 0 | 7 | 0 | 0 |
| Normal epithelium | 7 | 0 | 0 | 0 | 7 |
| Primary cancer | 7 | 0 | 2 | 4 | 1 |
| Lymph node metastases | 4 | 0 | 3 | 1 | 0 |

$n^a$ number of specimens examined.

The identification of the LO gene as one that is differentially expressed in metastatic prostate tissue as compared to primary tumor and normal tissue reveals the usefulness of LO in diagnostic and treatment protocols according to the present invention provides a novel cancer progression/metastasis-related candidate gene for further studies. Because low LO expression levels correlate with metastasis, LO gene expression is useful as a prognostic marker for staging the metastatic state of a tumor and for monitoring a patient, such as a prostate cancer patient, after surgical treatment. The LO gene is also useful as a therapeutic agent. The LO gene, or a portion thereof, may be cloned into an expression system, such as, for example, an adenoviral vector, an adeno-associated viral vector, a lentiviral vector or a retroviral vector, and targeted for expression in a metastatic tumor, such as a metastatic prostate tumor, to suppress the metastatic potential of the tumor.

The LO gene product has been previously described as a copper-dependent enzyme expressed predominantly in bone, blood vessels, and connective tissue, and leads to the stabilization of matrix structure by cross-linking collagen and elastin in the extracellular matrix (Kagan, H. M., In: Regulation of Matrix Accumulation, R. P. Mecham (ed.), Vol. 1, pp. 321–398. New York: Academic Press. 1986; Kagan, H. M., et al., Am. J. Respir. Cell Mol. Biol., 5: 206–210, 1991). Expression of LO has been reported to be stimulated by TGF-β1 in osteoblasts, vascular smooth muscle cells and lung fibroblasts (Feres-Filhot, E J, et al., JBC 270:30797–30803, 1995; Shanley, C J, et al., J. Vasc. Surg., 25:446–452, 1997; Boak, A. M., et al., Am. J. Respir. Cell Mol. Biol. 11:751–755, 1994). Increased LO activity has also been reported in fibrotic disorders, whereas decreased LO activity is associated with inherited disorders of collagen (Kivirikko, K I, et al., In J. Uitte and A. J. Pere (eds.), Connective Tissue Disease, pp. 263–292. New York: Marcel Dekker, Inc., 1987; Danks, D M, In: Connective Tissue and Its Heritable Diseases: Molecular, Genetic and Medical Aspects, P. M. Royce and B. Steinmann (eds.), pp. 487–506. New York:. Wiley-Liss, Inc. 1992; Kivirikko, K I, Ann. Med., 25:113–126, 1993).

Increased expression of the LO gene has also been reported for ras-transformed mouse fibroblasts which revert from a ras-transformed phenotype to a normal phenotype (Contente, S, et al., Science 249:796–798, 1990; Hajnal, A, et al., Cancer Res., 53:4670–4675, 1993). LO is also regulated by the anti-oncogenic transcription factor IRF-1 (Tan, R S, et al., Cancer Res., 56:2417–2421, 1996) indicating that LO may function as a tumor suppressor. Low levels of LO mRNA have also been detected by RT-PCR in several human tumor cell lines (Kuivaniemi, H, et al., FEBS Lett., 195:261–264, 1986; Hämäläinen, E, et al., J. Biol. Chem., 270:21590–21593, 1995). Additionally, LO expression has been detected in the extracellular matrix of breast cancer cells (Peyrol, S, et al., Am. J. Pathol., 150:497–507, 1997).

As demonstrated herein, the LO gene has been identified for the first time to be a TGF-β1-induced gene in primary tumor-derived cell lines, but not in cells derived from a genetically matched metastatic counterpart tumors. Northern blotting analysis of a panel of primary tumor cell lines revealed increased LO expression, but significantly reduced or nondetectable LO expression in their genetically matched metastatic counterparts. Further analysis using in situ hybridization revealed expression of the LO gene in normal mouse prostate epithelium but, in most cases, progressive loss of expression in primary prostate cancer and associated metastatic lesions. The progressive loss of LO expression during prostate cancer progression provides information that may increase understanding of the mechanisms that underlie this disease. Furthermore, LO gene expression may now serve as a useful molecular marker and/or a novel therapeutic target for prostate cancer. Accordingly, administration of LO or a functional equivalent of LO may be used as a therapeutic in the treatment of metastatic disease and other neoplastic disorders.

The invention is the first documentation of LO expression in normal prostate cells vs. prostate cancer cells. LO mRNA is present predominantly in epithelium and, to a lesser extent, in the stromal cells of normal mouse and human prostatic tissues. This information adds to the limited understanding of the localization of LO and glandular tissues in general. Previous studies of the expression and regulation of LO have been carried out predominantly using stromal-derived cell lines (Feres-Filhot, EJ, et al., JBC 270: 30797–30803, 1995; Shanley, C J, et al., J. Vasc. Surg., 25: 446–452, 1997; Boak, A M, et al., Am. J. Respir. Cell Mol. Biol. 11: 751–755, 1994; Contente, S, et al., Science 249: 796–798, 1990; Hajnal, A, et al., Cancer Research 53: 4670–4675, 1993; Tan, R S, et al., Cancer Research. 56: 2417–2421, 1996; Kuivaniemi, H, et al., FEBS Lett., 195: 261–264, 1986; Hämäläinen, E R, et al, JBC 270: 21590–21593, 1995).

Studies of LO expression in malignant human breast tissues have been reported (Peyrol, S. et al., Am. J. Pathol., 150:497–507, 1997). In the Peyrol study, LO was undetectable in normal breast tissue using immunostaining for LO protein. However, in situ hybridization analysis for LO demonstrated that the presence of mRNA in stromal cells surrounding glandular epithelium and reduced LO expression was associated with loose or scirrhous stroma that accompanied invading tumors (Peyrol, S, et al., Am. J. Pathol., 150:497–507, 1997.)

The present studies on prostate cancer progression also associate with loss of LO expression with cancer progression. In the case of prostate cancer, the malignant cells per se demonstrate a progressive reduction in LO mRNA during primary tumor development and metastasis. Studies are currently ongoing to further define the compartmentalization of LO in normal and malignant prostate and to better understand its biological and clinical significance. Although results indicate loss of LO mRNA during mouse and human prostate cancer progression, the molecular basis for this loss is less clear. Alterations may occur not only in the expression of the LO gene, but also in the anti-oncogenic transcription factor IRF-1 which regulates expression (Tan, R S, et al., Cancer Research 56:2417–2421, 1996).

These results have implications for the biological underpinnings of prostate cancer progression. It has been previously suggested that the protective effect of a collagenized matrix might be determined by collagen cross-linking which could dictate fibrillar and basement membrane stability against metalloproteinase activities (Vater, C A, Biochem. J., 181:639–635, 1979). This concept was recently supported by studies involving invasive ductal breast carcinoma (Peyrol, S, et al., Am. J. Pathol., 150:497–507, 1997). This protective effect may underlie, in part, the phenomenon associated with the reversion of ras-transformed 3T3 cells by LO (Contente, S, et al., Science 249:796–798, 1990; Hajnal, A, et al., Cancer Res., 53:4670–4675, 1993). In addition to promoting a physical extracellular matrix cross-linking barrier against malignant progression, it is also conceivable that maintaining the integrity of the extracellular matrix prevents the release of mitogenic growth factors (Thompson, K, et al., J. Cell. Physiol. 166:495–505, 1996). These concepts are now relevant for prostate cancer progression. Progressive loss and/or unusual patterns of LO expression in prostate cancer biopsy material may be of prognostic significance. The LO gene can now be considered a potential tumor suppressor gene or component of a tumor suppressor pathway for prostate cancer and, therefore, a target for molecular therapeutic strategies.

In addition, as discussed in below in the examples, LO expression is an independent prognostic factor for prostate cancer recurrence, indicating that it plays a role in prostate cancer progression. Thus, this novel marker will likely have clinical significance for predicting prostate cancer recurrence in various clinical settings.

Additional Operations

Selected potential therapeutic and diagnostic uses of the invention include:

1. Antisense Therapy: An antisense sequence, such as an antisense caveolin sequence, may be used for a number of applications, including antisense blocking or antisense inhibition. Antisense blocking refers to the incorporation into a cell of expression sequences which direct the synthesis of antisense nucleic acid to block expression of a target gene. Antisense hybridizes to the mRNA of the target gene to inhibit expression.

Antisense inhibition also exploits the specificity of hybridization reactions between two complementary nucleic acid chains to suppress gene expression. If a cloned gene is engineered so that only the opposite DNA strand is transcribed, the resultant RNA may hybridize to the sense RNA and inhibit gene expression.

2. Domain-specific uses: Some of the identified metastatic sequences may encode polypeptides with domains useful in specific applications. For example, there are three genes in the caveolin family, caveolin-1, caveolin-2 and caveolin-3. Two domains have been identified on caveolin-1 that have important biological functions. One of these domains mediates dimerization between caveolin-1 and caveolin-2. This dimerized form of caveolin spontaneously leads to the formation of caveolae. The other domain, the scaffolding domain, mediates the binding of some, but certainly not all, of the specific proteins that can initiate signal transduction. These sites on caveolin can serve as potential targets for drugs or peptides that interfere with or modify these biological activities. For example, these sequence sites could be the subject of gene targeting or other diagnostic and therapeutic strategies.

3. Interference peptides: In addition, small interference peptides may be chemically linked to steroids to allow for both specificity of cell target as well as the specificity of intercellular pathway.

4. Viral vectors and non-viral approaches: Specific treatment approaches using metastatic sequences may include the delivery of sense, antisense or dominant negative forms of metastatic sequences such as caveolin, lysyl oxidase or p99, using expression or viral vectors or non-viral approaches.

5. Gene promoter approaches: The gene promoter, for example, the caveolin gene promotor, which has been cloned, can be used for cell targeting of the expression of therapeutic gene sequences. The prostate cancer cells expressing high levels of caveolin, and possibly the breast cancer cells expressing high caveolin levels, are the cells that are more likely to metastasize, because they can survive in the vasculature and lymphatic system where concentrations of growth factors and testosterone are very low compared to the prostate per se. In addition, the normal blood vessel endothelium expresses high levels of caveolin; thus, the killing of these cells would promote overall tumor death. Because the caveolin promoter appears to be highly up regulated in metastatic cells, it is an advantageous promoter for use in driving the expression of therapeutic gene sequences. The therapeutic genes sequences could be lysyl oxidase, antisense caveoli, antisense p99, or other sequences with anti-metastatic properties.

6. Metastatic sequences as biomarkers: Metastatic sequences, such as lysyl oxidase and caveolin may have applications as biomarkers. For example, caveolin is up-regulated by cholesterol, insulin-like growth factor 1 and testosterone. As these factors may be risk-factors for the development and/or progression of prostate and breast cancer, sequences caveolin may serve as an intermediate biomarker for the adverse effects of these dietary/hormonal elements.

Caveolin levels in African-American prostate cancer are four times higher than that in Caucasian prostate cancer, which has been controlled for stage and grade of cancer. African-Americans have a much higher rate of progression and mortality from prostate cancer than Caucasians.

The caveolin promoter (in the mouse gene) has an unusual region of di-nucleotide and tri-nucleotide repeats that could be highly mutable. This may explain the "genetic difference" in caveolin expression in African Americans versus Caucasians in response to, perhaps, dietary cholesterol.

Lysysl oxidase is down-regulated in metastatic cells and may thus be useful as a marker for metastasis. The LO biomarker would have application in monitoring patients, for example, a prostate cancer patient, after surgical treatment methods, or for staging cancer progression of a tumor, such as a prostate primary tumor.

7. Gene transfer-initiated "in vivo priming" of tumor infiltrating lymphocytes: Solid tumors attract lymphocytes that migrate into the tumor and initiate various levels of antitumor activities. These tumor infiltrating lymphocytes, or TILs, reflect, as well as alter, the biological milieu of the tumor and potentially have the capacity to destroy tumor cells if sufficient activation levels are achieved. Previously, methodologies have been developed for the isolation of TILs from solid tumors, their activation with specific cytokines in vitro and their administration to patients for potential therapeutic benefits. The results of multiple clinical trials using TIL therapies indicate that in a relatively low but consistent percentage of the patients, TIL therapy can result in measurable therapeutic benefits and in some cases outright cure of the disease. The reasons for this limited therapeutic activity of ex vivo activated TIL appear to be multifaceted and likely include: 1) the lack of substantial TIL recovery from the tumor that could reflect limited infiltration, 2) the limited activation state of the TIL recovered from tumors, and 3) the inability to fully ex vivo activate the TIL to the cytotoxic in vivo state.

Another embodiment of the invention is directed to compositions and methods that involve administration of viral vector-delivered gene therapies having immunomodulatory activities for cancer and, preferably, metastatic disease. These therapies include the delivery of the Herpes Simplex Virus thymidine kinase (HSV-tk) gene followed by the administration of systemic ganciclovir. This gene therapy approach results in hemorrhagic necrosis within the tumor that leads to high levels of lymphocytic infiltration and increased activity of specific lymphocytes including T cells. Based on these and other preliminary data, specific in vivo gene therapy approaches, in combination with TIL transfer, are expected to produce significantly enhanced therapeutic activities compared to current. TIL methods. The enhanced therapeutic activities will result from the "in vivo priming" that occurs in response to the activities of the transferred genes. This "in vivo priming" will produce: 1) enhanced lymphocytic infiltration and 2) a higher activated state of the infiltrating lymphocytes. A preferred embodiment of the present invention comprises pretreating a patient with adenoviral vector delivered HSV-tk+ganciclovir therapy, and possibly other cytokine genes, in combination with traditional TIL therapy to produce a distinct therapeutic advantage by increasing the amount of lymphocytic infiltration and activation state within the context of high levels of tumor antigen in vivo. This combination "in. vivo priming"/ TIL therapy approach may be used directly following surgery or biopsy, or the activated cells could be frozen for future use. Diagnostic and/or prognostic information may be recovered from the more fully expanded and activated cells.

8. Suppression of genes associated with the drug resistant phenotype: It is possible to increase the susceptibility of a tumor to drug treatment. There are genes, such as mdr1 and caveolin, that encode for proteins that confer a drug-resistant phenotype to cells. This drug-resisitant phenotype presents an obstacle in treatment due to the cells' insensitivity to cancer drugs. Therefore an approach to increase the susceptibility of these cells to cancer drugs is to decrease or suppress the expression of the multidrug resistance gene(s) combined with apoptosis-inducing drug therapy. This suppression of the drug resisitant genes could be via antibodies or antisense sequences.

9. Recombinant adenoviral vectors for gene therapy: overexpression of cyclin-dependent kinase inhibitors p18 and p19 using Adcp18 and Adcp19: Many human malignancies present therapeutic dilemmas for the clinician. Prostate cancer therapy is remarkable in this regard. The incidence of pathological prostate cancer is exceedingly high and with current methods of detection (primarily PSA screening) available hundreds of thousands of men are being diagnosed with prostate cancer. However, only a small percentage of these cancers would normally progress to clinical, significance. Yet the dominant therapy for these cancers is radical prostatectomy, a serious surgical procedure with significant associated risks. In addition the current modalities used to stage prostate cancer are not sufficiently accurate to be confident that the cancer has not metastasized from the primary tumor site. Currently there are no satisfactory treatments for metastatic prostate cancer. Therefore it is imperative to develop novel and effective therapies for localized prostate cancer that are less dangerous than radical surgery as well as novel and effective therapies for metastatic disease. In vivo gene therapy for prostate cancer has the potential to provide effective and relatively harmless therapy for both local and metastatic prostate cancer.

One gene therapy approach of the invention for the control of localized prostate cancer is to replace or increase the dose of genes that suppress the growth of malignant prostate cells. Previous studies have examined the effects of vector mediated gene transfer of the wild type p53 gene, a known G1->S checkpoint control gene. p53 has been shown to produce growth suppression through the transcriptional activation of p21, a cyclin dependent kinase inhibitor (CKI). More recently we and other laboratories have tested the therapeutic effects of p21 gene transfer (Eastham et al., Cancer Res. 55:5151–5155, 1995). The p21 protein is transcriptionally regulated by p53 and functions as a primary effector for arresting cells at the G1->S interface. Recently the concept of CKI-mediated gene therapy has been extended by constructing and testing two recombinant adenoviral vectors which transduce the p18 and p19, unique CKIs that may also have activity in malignant prostatic epithelium. Transcriptional regulation of p18 and p19 is under the transcriptional control of the cytomegalovirus promoter and the recombinant virus was generated by co-transfection of the expression cassette with Ad5 virus that had been previously digested with restriction endonucleases cleave the virus in the E1A region, allowing recombination to occur. These recombinant viruses have been tested for activity in mouse and human prostate cancer cells in vitro. The results indicate that both recombinant adenoviruses are capable of suppressing the growth of these cells. Further studies will test the activities of these recombinant viruses in prostate cancer in vivo to further define a role for these reagents in human gene therapy protocols.

The following experiments are offered to illustrate embodiments of the invention and should not be viewed as limiting the scope of the invention.

EXAMPLES

Example 1

Production of Mouse Prostate Reconstitution Tumors and Metastasis

Mouse Urogenital Sinus (UGS) tissue was isolated from 17 day old mice embryos. Each isolated UGS was digested with 1% trypsin for three hours at 4° C. The trypsin was inactivated by the addition of fetal calf serum. UGS cells were digested with 0.125% collagenase for 1.5 hours, counted and mixed at the appropriate cell rations prior to infection with retrovirus in the presence of polybrene. Retro viruses used include Zipras/myc-9. Control experiments were performed using BAGα virus. After a two-hour infection, the infected cells were centrifuged and individual reconstitutions containing $1.5 \times 10^6$ cells produced by resuspending the cells in rat tail collagen at a density of $6.0 \times 10^7$ cells per ml. Aliquots of the infected UGS cells were placed in (DME) with 10% fetal calf serum overnight at 37° C., 5% $CO_2$. The next morning each cell/collagen reconstitution was implanted under the renal capsule of an adult male. +/+ animal. Reconstitutions were harvested from the mice five weeks later when they showed signs of obvious distress from the tumor burden. Metastasized tumors were isolated from the same mice at sites outside the renal capsule. Isolated tumors and metastasises were either stored in liquid nitrogen or in preservatives such as 10% buffered formalin. Cell lines were derived from fresh tumors by mincing a small portion of the primary metastatic or nonmetastatic tumor and placing each in explant culture in Dulbecco's Modified Eagle Medium (DMEM) supplemented with 10% fetal calf serum. Cells which grow from each explant were propagated in DMEM and 10% fetal calf serum. For histological analysis, a portion of a fresh tumor was fixed in 10% buffered formalin and embedded in paraffin for sectioning and staining with hematoxylin and eosin (H&E) or immunohistochemical staining. Immunohistochemical localization of cytokeratin was detected using polyclonal cytokeratin antiserum A575 (Dake Co., Carpinteria, Calif.) and Vectastain ABC kit (Vector Laboratories, Burlingame, Calif.).

Example 2

Isolation of C-DNA for DD-PCR

Total cellular RNA was isolated by ultracentrifugation through cesium chloride. Briefly, up to one gram of cells from culture, tumors or organs was placed into 4 ml of ice-cold GIT buffer (4M guanidine isothiocyanate, 0.025 M sodium acetate, 0.1 M β-mercaptoethanol) and. homogenized in a tissue homogenizer (Polytron or equivalent). The homogenate was carefully layered over 4 ml of 5.7 M CsCl, 0.024 M sodium acetate (1.8 g CsCl per ml) in a centrifuge tube. The layers were centrifuged at 35,000 RPM for 18 hours in a SW50.1 rotor. DNA was collected from the interface between the cushion and the supernatant, diluted two folds with water, added to 2.5 volumes of ethanol and spooled out on a glass rod. RNA that formed a pellet on the bottom of the CsCl layer was resuspended, and once extracted with an equal volume of phenol:chloroform. (1:1), twice with chloroform and precipitated with ethanol and resuspended in diethylpyrocarbonate treated water. The concentration of DNA and RNA were be determined by absorption at 260 nanometers.

Example 3

Differential Display Polymerase Chain Reaction mRNA isolated from primary tumors or metastasis was reverse transcribed with one of the primers and subjected to DD-PCR using the same primer as both the forward and reverse primer. A set of 24 primers comprising short oligonucleotides were used for both the reverse transcription of mRNA into c-DNA and for differential display polymerase chain reaction.

PCR was performed using standard conditions with 40 cycles of denaturation at 94° C. for 40 seconds, annealing at 40° C. for 2 minutes, and elongation at 72° C. for 35 seconds. After PCR, the products were analyzed with non-denaturing polyacrylamide gel electrophoresis (PAGE) at 12 watts for 15 hours. Bands. which differed between test and control samples were eluted from the gel, subjected to reamplification by PCR and cloned. Northern blot analysis was performed showing that the sequence isolated by DD-PCR is differentially expressed.

Example 4 p53 Allelotype Determination

The p53 allelotype of a cell sample was determined by PCR. Briefly, nucleic acid is extracted from a tissue sample or a cell culture sample. An aliquot of nucleic acids in placed in 45 $\mu$l aliquot of a master mix which contained a final concentration of 0.2 mM of each dATP, dTTP, dGTP, dCTP, 1.5 mM $MgCl_2$, 0.5 unit Taq polymerase, 0.05 $\mu$M of each of two primers set specific for the normal wildtype allele of p53. A control set of primers specific for the fibroblast growth factor-7 gene was used to monitor the polymerase chain reaction experiment. One $\mu$l of the reaction from the first round of PCR was used as the starting material for a second round of PCR using a second set of wildtype p53 specific primer. This second round of PCR was also monitored using a control set of primers specific for the fibroblast growth factor-7. After PCR the products were analyzed with non-denaturing polyacrylamide gel electrophoresis (PAGE) at 12 watts for 15 hours. Bands which differed between test and control were eluted from the gel, subjected to reamplification by PCR and cloned.

Example 5

Induction of Cell Lines with TGF-β1 Influence Cellular Gene Expression

1481PA cells were grown overnight in DME supplemented with 10% fetal calf serum overnight at 37° C., and 5% $CO_2$. Induction was performed by treatment with TGF-β1 at a concentration of 2 ng/ml. The treated cells were returned to the incubator and cultured for 12 hours. After induction, cells were washed in phosphate buffered saline and harvested and concentrated by centrifugation. RNA was extracted from treated and untreated cells and subjected to DD-PCR. Differentially expressed bands detected by DD-PCR were cloned and differential expressions were confirmed using RNA blots. Subsequent cloning and sequencing identified the bands as ABP280 or filamin. One gene isolated showed differential expression in cells induced by TGF-β (clone 29), while a control probe on the same cell line showed no difference in expression levels (GAPDH). RNA blot analysis of total RNA (20 $\mu$g) from primary-tumor and metastasis derived cell lines in three independent mouse prostate reconstitutions (148-1, 151-1 & 151-2) showed differential expression. Control experiments using the same cell lines, but using a probe to GAPDH, showed no differential expression.

Example 6

Metastatic Sequences Isolated

Using the methods of Examples 1, 2, 3, 4, and 5, a plurality of metastatic sequences were isolated and sequenced. The expression of the metastatic sequences in primary cells and in metastatic cells were determined using RNA blots. The results of these studies are summarized in FIG. 9.

Example 7

Caveolin Immunoassay in Human Prostate Cancers

Primary site human prostate tumors and metastases were isolated and analyzed for caveolin expression by immunoassay. The results of the assay is shown in Table 2 Metastases shows higher levels of caveolin proteins in metastases than in primary tumors. Immunohistology of tissue sections reveals both elevated levels and distinct distribution of caveolin protein in metastatic human prostate when compared to a primary human prostate tumor.

TABLE 2

| Patients | Primary-site | Metastases in lymph node |
| --- | --- | --- |
| 1 | + | ++ |
| 2 | ++ | +++ |
| 3 | ++ | +++ |
| 4 | ++ | ++ |
| 5 | + | + |
| 6 | ++ | ++ |
| 7 | ++ | +++ |
| 8 | + | + |
| 9 | − | − |
| 10 | + | + |
| 11 | + | + |
| 12 | ++ | ++ |
| 13 | + | + |
| 14 | ++ | +++ |

Example 8

Production of Primary and Metastatic Mouse Prostate Cancer Cell Lines

Mouse prostate cancer cell lines were derived from primary tumors or metastatic deposits in the same host animal implanted with a ras+myc-initiated p53-nullizygous MPR (Thompson, T C, et al., Oncogene, 10: 869–879, 1995). The cell lines were analyzed for retroviral integration patterns by Southern blotting (Thompson, T C, et al., Oncogene, 10:869–879, 1995) and cultured as described previously (Sehgal, L, et al., Cancer Res., 56:3359–3365, 1996). All murine cell lines were used at early passages, i.e., passages 7–10. The primary tumor-derived cell line 148-IPA was seeded into 15-cm diameter plates at $3\times10^6$ cells per plate, and the next day, the medium changed to SFM (serum-free medium, which was DMEM with 10 mM HEPES, penicillin, streptomycin, and 0.1% BSA), without or with 2 ng/ml TGF-β1, and the cells were incubated at 37° C. for 12 or 24 hours.

Example 9

Isolation and Analysis of RNA

RNA was isolated from cell lines as described previously (Thompson, T C, et al., Oncogene, 10:869–879, 1995), or with commercially available RNA isolation reagents (Biotex). mRNA was purified from total RNA with PolyAT-tract mRNA Isolation System (Promega). For Northern blot analysis, 20 μg of total RNA were fractionated under denaturing conditions on a 1% agarose-6.7% formaldehyde gel and transferred onto Hybond-N nylon membrane (Amersham). The membrane was baked at 80° C. for 2 hours prior to prehybridization at 65° C. for 2 hours in 7.5% SDS, 0.5 M sodium phosphate buffer (pH 7.2), 1 mM EDTA, 4×Denhardt's solution (50×Denhardt's solution=1% Ficoll, 1% polyvinylpyrrolidone, and 1% BSA), and 50 μg/ml salmon testis DNA. Hybridization was carried out by addition of a $^{32}$P-labeled probe that had been purified with a QIAquick spin column (Qiagen). The hybridization was incubated overnight at 65° C. Blots were washed at 65° C. for 20 min with wash solution (40 mM sodium phosphate (pH 7.2), 5% SDS) two times.

Example 10

Differential Display Polymerase Chain Reaction

One of a set of unique 10-mer deoxyoligonucleotide primers, primer 11, with an arbitrarily chosen sequence (primer 11=CTGCTTGATG), was used for reverse transcription. Primer 11 was also used as both a 5' and 3' primer for amplification by PCR. The primers were selected based on having approximately the same G+C:A+T ratio, with no uninterrupted self-complementary sequence of more than 2 nucleotides (Ralph, D; et al., PNAS USA, 90:10710–10714, 1993.). Reverse transcription (RT) of mRNA was with the Perkin-Elmer/Cetus GeneAmp RNA PCR kit. The RT reaction volume was 10 μl and was contained in 5 mM MgCl$_2$, 1×PCR buffer II, 1 mM each dNTP (dATP, dCTP, dGTP, and dTTP), 1 unit/μl RNase inhibitor, 2.5 units/μl reverse transcriptase, 250 nanograms of primer, and 60 nanograms of mRNA. The reaction mixture was covered with 50 μl of mineral oil and incubated at 22° C. for 10 min, 42° C. for 15 minutes, and 99° C. for 5 minutes (termination). The reaction was immediately diluted to 50 μl and adjusted such that it contained 2 mM MgCl$_2$, 1×PCR buffer II, 1.25 units of AmpliTaq DNA polymerase, and 20 μCi of [$^{33}$P]dATP (3000 Ci/mmol). No additional dNTPs or primer were added, so that the final concentrations were 0.2 mM each dNTP and 250 negotiating of primer. The PCR consisted of 40 cycles at 94° C. for 40 seconds, 40° C. for 2 minutes, and 72° C. for 35 seconds, with a final extension period of 72° C. for 4 minutes.

Samples from the PCR were separated on a nondenaturing 5% polyacrylamide gel (29:1) with 5% glycerol at 9 W for 18 hours. The gel was transferred to Whatman 3 MM paper, dried, and exposed to X-ray film overnight. The differentially displayed bands were excised from the dried polyacrylamide gel and soaked in 500 μl of H$_2$O for 15 min at room temperature to remove the filter paper, and the gel slice was transferred to 20 μl of 10 mM Tris (pH-8)-1 mM EDTA buffer, smashed, and incubated at room temperature from 2 h to overnight. A 5-μl aliquot was reamplified in a 50-μl PCR mixture containing 1×PCR buffer II, 2 mM MgCl$_2$, 0.25 mM dNTP, 1.25 units of AmpliTaq DNA polymerase, and 1 μg of primer. The PCR was 45 cycles, with the same parameters as above. The reamplified cDNA fragments were purified on 2% NuSieve agarose (FMC Bioproducts) by gel electrophoresis. The bands were excised and used to make a $^{32}$P-labeled probe for Northern blot analysis as described above or cloned into TA cloning vector (PCR 2.0 vector; Invitrogen). The cloned DD-PCR fragments were sequenced with Sequenase Version 2.0 (United States Biochemical).

Example 11

Histological Analysis of RNA Expression

Frozen sections 6 μm thick from normal mouse prostate and mouse prostate cancer and lymph nodes with metastatic deposits produced in the MPR system were used for in situ hybridization. In addition, frozen sections 6 μm thick from seven histologically normal human prostates obtained from cystoprostatectomy specimens and seven primary cancers from radical prostatectomies, together with their lymph node metastases (four of seven cases), were also analyzed. Sections were air-dried and fixed in a fixative containing 2% paraformaldehyde, 75% ethanol, and 23% acetic acid for 30 min. After treatment with 0.2 N HCl for 10 min, the slides were digested for 20 min in 5 μg/ml proteinase K, rinsed in 0.2 mM glycine/PBS, and fixed for 20 min in 4% paraformaldehyde, Antisense (cRNA of LO) or sense RNA probes were obtained by run-off transcription of the vector pCR 2.0 (Invitrogen), into which the 307 bp fragment of the mouse LO cDNA had been subcloned. The recombinant DNAs were linearized with HindIII or XbaI. The sense and antisense probes were prepared with T7 or SP6 polymerase, respectively, using the DIG (digoxigenin) RNA labeling kit from Boehringer Mannheim by SP6/T7 transcription, according to the procedure recommended by the manufacturer. The sections were prehybridized in 50% formamide, 5×SSC, 5×Denhardt's solution,. 250 μg/ml yeast t-RNA, 4 mM EDTA, and 1 mg/ml salmon sperm DNA for 60 minutes at 37° C. and hybridized in the prehybridization buffer (without the salmon sperm DNA) containing 20 negotiating/μl DIG-labeled cRNA probes at 48° C. for 16 hours. Following washing in 4×SSC for 20 minutes, the sections were digested with 20 μg/ml RNase A at 37° C. for 20 minutes, followed by further washing in 2×SSC (10 minutes), 1×SSC (20 minutes), and 0.1×SSC (30 minutes) at 48° C. DIG-labeled hybrids on sections were immunocytochemically detected by using an anti-DIG IgG conjugated with fluorescein (Boehringer Mannheim). Sections from primary and metastatic cancers were always processed in parallel on the same slides using the same batches of probes and reagents.

Example 12

Reduction of LO Expression as an Independent Predictor of Recurrence Following Radical Prostatectomy As noted, lysyl oxidase has enzymatic activity that can stabilize extracellular matrix and may have tumor suppressor activities. LO mRNA is predominantly expressed in normal mouse and human prostatic epithelial cells and to a lesser extent in prostatic stroma and that LO mRNA levels were significantly reduced in primary prostate cancer and further reduced in metastatic lesions. In this example, immunohistochemical (IHC) staining was used to analyze LO in human prostate cancer specimens. Specifically, sixty-one specimens obtained from radical prostatectomies were analyzed by IHC staining using the avidin-biotin complex technique in conjunction with a polyclonal LO antibody. LO-positive cancer cells were counted and expressed as a percent of cancer cell population. LO positive cancer cells were found to have heterogeneous distribution and LO levels in cancer were remarkably lower when compared with their adjacent, histologically normal glandular epithelia. LO labeling rates in cancers tended to decrease with increasing Gleason sum, although the differences did not reach statistical significance (p=0.088). No significant differences in LO levels were found in regard to seminal vesicle involvement, surgical margin status and lymph node metastases. However, a highly significant association was found between reduced LO positive cells and recurrence of cancer following radical prostatectomy (p=0.0041). Multivariate logistic regression analyses were performed to assess the effects of LO labeling rate, Gleason sum, lymph node metastases, surgical margins and seminal vesicle involvement as possible prognostic markers for recurrence. It was found that LO positive cells (p<0.042) as well as Gleason sum (p<0.016) added independent prognostic information. This demonstrates that LO expression is an independent prognostic factor for prostate cancer recurrence, suggesting that it plays a role in prostate cancer progression. This novel marker may be used to predict prostate cancer recurrence in various clinical settings.

Other embodiments and uses of the invention will be apparent to those skilled in the art from consideration of the specification and practice of the invention disclosed herein. All documents cited herein including U.S. Pat. No. 5,783,182, entitled "Method for Identifying Metastatic Sequences," which issued Jul. 21, 1998, and U.S. Provisional Patent Application, entitled Metastatic Sequences, serial number 60/077,934, filed Mar. 13, 1998, are specifically incorporated by reference. The specification and examples should be considered exemplary only with the true scope and spirit of the invention indicated by the following claims.

We claim:

1. An isolated nucleic acid comprising at least one sequence selected from the group consisting of: SEQ ID NO: 1; and the complement of SEQ ID NO 1.

2. A nucleic acid which consists essentially of a sequence selected from the group consisting of: SEQ ID NO: 1; the complement of SEQ ID NO 1.

3. The nucleic acid of claim 1 which encodes the polypeptide of SEQ ID NO: 2.

4. The nucleic acid sequence of claim 1 further comprising one or more additional sequences selected from the group consisting of promoter sequences, anti-sense message sequences, recombinant sequences for gene targeting, selectable marker sequences, replication origins, suppressor sequences and transcription and translation control sequences.

5. The nucleic acid sequence of claim 1 further comprising a gene that encodes a cytotoxic agent.

6. The nucleic acid of claim 5 wherein the cytotoxic agent is selected from the group consisting of cytokines, cytotoxic proteins, hormones, suppressor proteins, immunomodulating proteins and functionally-active portions and combinations thereof.

7. The nucleic acid of claim 6 wherein the hormone is an androgen.

8. A recombinant vector containing the nucleic acid sequence of claim 1.

9. The vector of claim 8 which is selected from the group consisting of eukaryotic, prokaryotic or viral vectors.

10. A liposome vesicle containing the nucleic acid sequence of claim 1.

11. The vesicle of claim 10 which comprises unilamellar phospholipids.

12. The vesicle of claim 10 further containing a toxic agent.

13. A kit for the detection of neoplasia comprising a nucleic acid comprising at least one sequence selected from the group consisting of: SEQ ID NO: 1 and the complement of SEQ ID NO: 1, further comprising one or more of salts, buffers, preservatives, or carriers.

14. The kit of claim 13 wherein the sequence is DNA or PNA.

* * * * *